(12) United States Patent
Isaacson et al.

(10) Patent No.: US 12,364,842 B2
(45) Date of Patent: *Jul. 22, 2025

(54) ACTIVATOR ATTACHMENT FOR BLOOD CONTROL CATHETERS

(71) Applicant: Becton, Dickinson and Company, Franklin Lakes, NJ (US)

(72) Inventors: S. Ray Isaacson, Layton, UT (US); Richard Champion Davis, III, Colorado Springs, CO (US); Bryan G. Davis, Sandy, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 672 days.

This patent is subject to a terminal disclaimer.

(21) Appl. No.: 17/396,474

(22) Filed: Aug. 6, 2021

(65) Prior Publication Data

US 2021/0361911 A1 Nov. 25, 2021

Related U.S. Application Data

(60) Continuation of application No. 16/156,559, filed on Oct. 10, 2018, now Pat. No. 11,135,399, which is a
(Continued)

(51) Int. Cl.
*A61M 39/06* (2006.01)
*A61B 5/15* (2006.01)
(Continued)

(52) U.S. Cl.
CPC ..... *A61M 25/0097* (2013.01); *A61B 5/15003* (2013.01); *A61B 5/150992* (2013.01);
(Continued)

(58) Field of Classification Search
CPC ........ A61M 39/0693; A61M 2039/268; A61M 25/0606; A61M 39/0606; A61M 25/0097;
(Continued)

(56) References Cited

U.S. PATENT DOCUMENTS

| 4,296,949 A | 10/1981 | Muetterties et al. |
| 4,387,879 A | 6/1983 | Tauschinski |

(Continued)

FOREIGN PATENT DOCUMENTS

| CA | 2 133 053 A1 | 3/1995 |
| CN | 202844313 | 4/2013 |

(Continued)

OTHER PUBLICATIONS

Elson Silva, PhD, "Respecting Hydrology Science in the Patenting System," pp. 1-7, Jan. 13, 2011.

*Primary Examiner* — William R Carpenter
*Assistant Examiner* — Robert F Allen
(74) *Attorney, Agent, or Firm* — Kirton McConkie; Whitney Blair; Kevin Stinger

(57) ABSTRACT

An activator attachment that can be attached to the proximal end of a catheter adapter and can activate a blood control valve within the catheter adapter.

12 Claims, 14 Drawing Sheets

Related U.S. Application Data division of application No. 15/155,311, filed on May 16, 2016, now Pat. No. 10,118,017, which is a continuation of application No. 13/644,217, filed on Oct. 3, 2012, now Pat. No. 9,358,364.

(60) Provisional application No. 61/544,179, filed on Oct. 6, 2011.

(51) Int. Cl.
| | |
|---|---|
| *A61M 25/00* | (2006.01) |
| *A61M 25/06* | (2006.01) |
| *A61M 39/00* | (2006.01) |
| *A61M 39/04* | (2006.01) |
| *A61M 39/22* | (2006.01) |
| *A61M 39/26* | (2006.01) |

(52) U.S. Cl.
CPC .... *A61M 39/0606* (2013.01); *A61M 39/0693* (2013.01); *A61M 25/0606* (2013.01); *A61M 2039/0036* (2013.01); *A61M 39/045* (2013.01); *A61M 2039/0633* (2013.01); *A61M 2039/064* (2013.01); *A61M 2039/066* (2013.01); *A61M 39/22* (2013.01); *A61M 2039/266* (2013.01); *A61M 2039/268* (2013.01)

(58) Field of Classification Search
CPC ............... A61M 39/045; A61M 39/22; A61M 2039/0036; A61M 2039/0633; A61M 2039/064; A61M 2039/066; A61M 2039/266
See application file for complete search history.

(56) References Cited

U.S. PATENT DOCUMENTS

| | | | |
|---|---|---|---|
| 4,449,693 A | 5/1984 | Gereg | |
| 4,758,225 A | 7/1988 | Cox et al. | |
| 4,773,552 A | 9/1988 | Boege et al. | |
| 4,781,702 A | 11/1988 | Herrli | |
| 4,809,679 A | 3/1989 | Shimonaka et al. | |
| 4,842,591 A | 6/1989 | Luther | |
| 4,874,377 A | 10/1989 | Newgard et al. | |
| 4,917,668 A | 4/1990 | Haindl | |
| 4,935,010 A | 6/1990 | Cox et al. | |
| 4,950,257 A | 8/1990 | Hibbs et al. | |
| 5,041,097 A | 8/1991 | Johnson | |
| 5,053,014 A | 10/1991 | Van Heugten | |
| 5,062,836 A | 11/1991 | Wendell | |
| 5,064,416 A | 11/1991 | Newgard et al. | |
| 5,084,023 A | 1/1992 | Lemieux | |
| 5,085,645 A | 2/1992 | Purdy et al. | |
| 5,098,405 A | 3/1992 | Peterson et al. | |
| 5,108,374 A | 4/1992 | Lemieux | |
| 5,127,905 A | 7/1992 | Lemieux | |
| 5,154,703 A | 10/1992 | Bonaldo | |
| 5,156,596 A | 10/1992 | Balbierz et al. | |
| 5,176,652 A | 1/1993 | Littrell | |
| 5,234,410 A | 8/1993 | Graham et al. | |
| 5,242,423 A | 9/1993 | Goodsir et al. | |
| 5,269,771 A | 12/1993 | Thomas et al. | |
| 5,290,246 A | 3/1994 | Yamamoto et al. | |
| 5,295,969 A | 3/1994 | Fischell et al. | |
| 5,330,435 A | 7/1994 | Vaillancourt | |
| 5,350,363 A | 9/1994 | Goode et al. | |
| 5,352,205 A | 10/1994 | Dales et al. | |
| 5,376,077 A | 12/1994 | Gomringer | |
| 5,405,323 A | 4/1995 | Rogers et al. | |
| 5,456,675 A * | 10/1995 | Wolbring | A61M 5/158 604/537 |
| 5,474,544 A | 12/1995 | Fynn | |
| 5,487,728 A | 1/1996 | Vaillancourt | |
| 5,520,666 A | 5/1996 | Choudhury et al. | |
| 5,549,566 A | 8/1996 | Elias et al. | |
| 5,549,577 A | 8/1996 | Siegel et al. | |
| 5,575,769 A | 11/1996 | Vaillancourt | |
| 5,613,663 A | 3/1997 | Schmidt et al. | |
| 5,651,772 A | 7/1997 | Arnett | |
| 5,653,698 A | 8/1997 | Niedospial et al. | |
| 5,657,963 A | 8/1997 | Hinchliffe et al. | |
| 5,697,915 A | 12/1997 | Lynn | |
| 5,738,144 A | 4/1998 | Rogers | |
| 5,749,861 A | 5/1998 | Guala et al. | |
| 5,772,643 A | 6/1998 | Howell et al. | |
| 5,806,831 A | 9/1998 | Paradis | |
| 5,817,069 A | 10/1998 | Arnett | |
| 5,833,674 A | 11/1998 | Turnbull et al. | |
| 5,911,710 A | 6/1999 | Barry et al. | |
| 5,954,698 A | 9/1999 | Pike | |
| 5,967,490 A | 10/1999 | Pike | |
| 6,039,302 A | 3/2000 | Cote, Sr. et al. | |
| 6,077,244 A | 6/2000 | Botich et al. | |
| 6,117,108 A | 9/2000 | Woehr et al. | |
| 6,171,287 B1 | 1/2001 | Lynn et al. | |
| 6,273,869 B1 | 8/2001 | Vaillancourt | |
| 6,287,280 B1 | 9/2001 | Lampropoulos et al. | |
| 6,319,236 B1 | 11/2001 | Bock | |
| 6,485,473 B1 | 11/2002 | Lynn | |
| 6,575,960 B2 | 6/2003 | Becker et al. | |
| 6,595,981 B2 | 7/2003 | Huet | |
| 6,699,221 B2 | 3/2004 | Vaillancourt | |
| 6,719,726 B2 | 4/2004 | Meng et al. | |
| 6,740,063 B2 | 5/2004 | Lynn | |
| 6,883,778 B1 | 4/2005 | Newton et al. | |
| 7,008,404 B2 | 3/2006 | Nakajima | |
| 7,347,839 B2 | 3/2008 | Hiejima | |
| 7,396,346 B2 | 7/2008 | Nakajima | |
| 7,470,254 B2 | 12/2008 | Basta et al. | |
| 7,682,340 B2 | 3/2010 | Funamura et al. | |
| 7,736,339 B2 | 6/2010 | Woehr et al. | |
| 7,914,494 B2 | 3/2011 | Hiejima | |
| 8,951,230 B2 | 2/2015 | Tanabe et al. | |
| 9,138,252 B2 | 9/2015 | Bierman et al. | |
| 9,358,364 B2 * | 6/2016 | Isaacson | A61B 5/15003 |
| 10,118,017 B2 * | 11/2018 | Isaacson | A61M 39/0606 |
| 11,135,399 B2 * | 10/2021 | Isaacson | A61M 39/0693 |
| 2005/0051572 A1 * | 3/2005 | Vogel | A61J 1/18 222/83 |
| 2006/0155245 A1 | 7/2006 | Woehr | |
| 2006/0163515 A1 | 7/2006 | Ruschke | |
| 2007/0083157 A1 | 4/2007 | Belley et al. | |
| 2007/0083162 A1 | 4/2007 | O'Reagan et al. | |
| 2007/0233007 A1 | 10/2007 | Adams | |
| 2008/0039796 A1 | 2/2008 | Nakajima | |
| 2008/0108944 A1 | 5/2008 | Woehr et al. | |
| 2008/0287921 A1 | 11/2008 | Bennett | |
| 2009/0281525 A1 * | 11/2009 | Harding | A61M 39/0613 604/537 |
| 2009/0287154 A1 | 11/2009 | Harding et al. | |
| 2010/0204648 A1 * | 8/2010 | Stout | A61M 39/0208 604/122 |
| 2010/0204675 A1 | 8/2010 | Woehr et al. | |
| 2010/0222746 A1 | 9/2010 | Burkholz | |
| 2011/0046570 A1 | 2/2011 | Stout et al. | |
| 2011/0160662 A1 | 6/2011 | Stout et al. | |
| 2011/0160663 A1 * | 6/2011 | Stout | A61M 25/0693 604/122 |
| 2012/0016301 A1 * | 1/2012 | Stout | A61M 25/0693 604/122 |
| 2012/0016302 A1 * | 1/2012 | Stout | A61M 25/0693 604/122 |
| 2012/0059325 A1 * | 3/2012 | Cluff | A61M 25/0606 29/460 |

(56) References Cited

U.S. PATENT DOCUMENTS

| | | | |
|---|---|---|---|
| 2012/0184912 A1* | 7/2012 | Cluff | A61M 25/0009 604/165.02 |
| 2012/0232498 A1* | 9/2012 | Ma | A61M 39/24 604/256 |

FOREIGN PATENT DOCUMENTS

| | | |
|---|---|---|
| DE | 20 2009 009 602 U1 | 12/2009 |
| EP | 0 369 314 A2 | 5/1990 |
| EP | 0 440 426 A1 | 8/1991 |
| EP | 0 968 736 A1 | 1/2000 |
| EP | 1 129 740 A2 | 9/2001 |
| EP | 1 679 043 A1 | 7/2006 |
| EP | 2489393 | 8/2012 |
| JP | 08-219314 | 8/1996 |
| JP | 2000-140526 | 5/2000 |
| JP | 2001046507 | 2/2001 |
| JP | 2001-526548 | 12/2001 |
| JP | 2002-263197 | 9/2002 |
| JP | 2003525660 | 9/2003 |
| JP | 2006102254 | 4/2006 |
| JP | 2008-173206 | 7/2008 |
| WO | 93/11696 | 6/1993 |
| WO | 96/41649 | 12/1996 |
| WO | 98/00195 | 1/1998 |
| WO | 99/34849 | 7/1999 |
| WO | 99/38562 | 8/1999 |
| WO | 2006/037638 A1 | 4/2006 |
| WO | 2006/059540 | 6/2006 |
| WO | 2007044878 A2 | 4/2007 |
| WO | 2008/014436 A2 | 1/2008 |
| WO | 2008/052790 A2 | 5/2008 |
| WO | 2009/114833 A1 | 9/2009 |
| WO | 2010/093791 A1 | 8/2010 |
| WO | 2011/046180 | 4/2011 |
| WO | 2012/002015 A1 | 1/2012 |

* cited by examiner

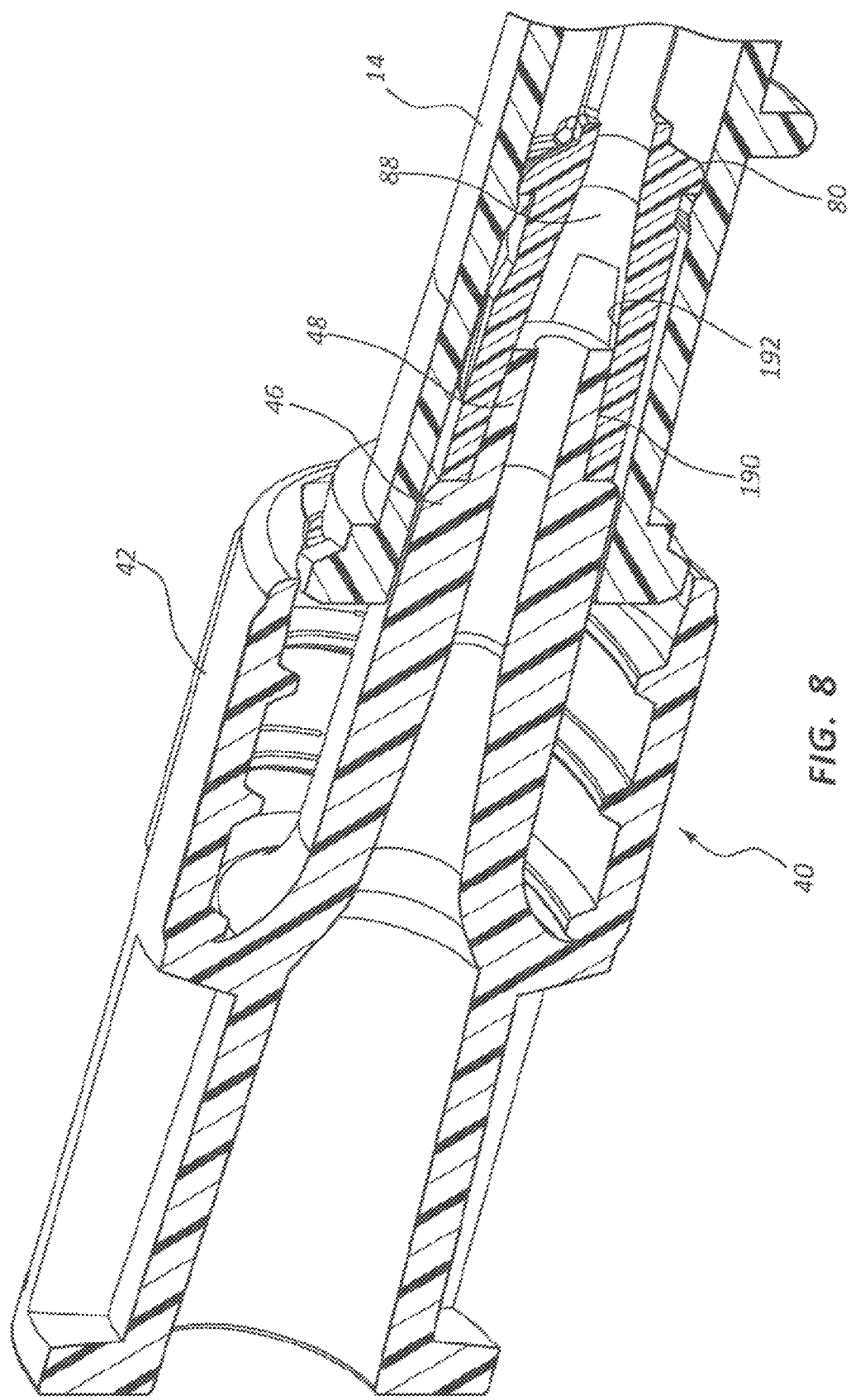

ACTIVATOR ATTACHMENT FOR BLOOD CONTROL CATHETERS

RELATED APPLICATIONS

This application is a continuation of U.S. patent application Ser. No. 16/156,559, filed Oct. 10, 2018, and titled ACTIVATOR ATTACHMENT FOR BLOOD CONTROL CATHETERS, which is a divisional of U.S. patent application Ser. No. 15/155,311, filed May 16, 2016, and titled ACTIVATOR ATTACHMENT FOR BLOOD CONTROL CATHETERS, which is a continuation of U.S. patent application Ser. No. 13/644,217, filed Oct. 3, 2012, and titled ACTIVATOR ATTACHMENT FOR BLOOD CONTROL CATHETERS, which claims the benefit of U.S. Provisional Application No. 61/544,179 filed Oct. 6, 2011, titled BLOOD DRAW AND GUIDEWIRE ADAPTER FOR BLOOD CONTROL CATHETERS, which are incorporated herein by reference.

BACKGROUND

The current invention relates to intravenous (IV) infusion devices, including IV catheters. In particular, the invention relates to an IV catheter assembly having a blood control valve therein and an activator attachment that attaches to the IV catheter assembly and activates the blood control valve to, for example, enable blood draw or aide in the insertion of secondary catheters and guide wires for longer dwell catheters.

IV catheters are commonly used for a variety of infusion therapies, including infusing fluids into a patient, withdrawing blood from a patient, or monitoring various parameters of the patient's vascular system. IV catheters are also used as introducing tools for longer dwell catheters such as Peripherally Inserted Central Catheters (PICC). The initial catheter is placed in the vascular system and then secondary catheters or guide wires are introduced into the vascular system using the pathway created by the initial catheter placement. The initial catheter which was used as an insertion guide is then removed, leaving only the longer term catheter in place.

Catheters are typically connected to a catheter adapter that accommodates the attachment of IV tubing to the catheter. Blood control catheter assemblies include an internal blood control valve that is opened by the insertion of a male luer or other object into a proximal end of the catheter adapter. Thus, following placement of the catheter into the vasculature of a patient, an IV fluid source can be connected to the catheter adapter, opening the blood control valve. Thus connected, fluid from the IV source can begin flow into a patient through the catheter.

Some catheter adapters permit verification of proper placement of the catheter in the blood vessel before fluid infusion begins, by providing a flashback chamber of the catheter assembly where a "flashback" of blood can be observed. To confirm flashback in catheter assemblies that do not include a blood control valve, a clinician must manually occlude the vein to prevent undesirable exposure to blood. In contrast, blood control valves can eliminate the need for such manual occlusion, while also reducing the likelihood of blood exposure during catheter placement.

Despite the many advantages of blood control catheters, some traditional procedures involving vascular access systems are not possible or are made more difficult with blood control catheters. Devices and systems that overcome these deficiencies are disclosed herein.

SUMMARY

The present invention has been developed in response to problems and needs in the art that have not yet been fully resolved by currently available systems and methods. In order to overcome the limitations discussed above, the present invention provides an activator attachment that can be selectively attached to a blood control catheter assembly to open its internal blood control valve and enables open access to the catheter and/or vasculature of the patient. Once such access is available, blood draws can be performed and secondary catheters and guide wires for longer dwell catheters can be inserted through the activator attachment. These processes are not advisable or possible within the attachment. For instance, blood control catheters alone do not allow blood to flow through the proximal end of the catheter device. Thus, blood sampling that is commonly done through the proximal open of the catheter is not available to clinicians. Moreover, the process of inserting a guide wire through a blood control catheter is complicated and not advisable since the guide wire can hit and possibly damage the septum or other features when the wire tip is inserted. Accordingly, the activator attachment can enable traditional procedures that are not possible or are made more difficult with blood control catheters.

In one aspect of the invention, an activator attachment includes an activator attachment body, a probe member of the activator attachment body, and a cannula coupled to the probe member. The activator attachment body has a distal end, a proximal end, and a lumen extending through these ends. The lumen has an unrestricted proximal opening. The lumen extends through the probe member, which is shaped and sized to be inserted within a proximal opening of a catheter adapter. The cannula has a length that is greater than the combined length of a septum activator and septum disposed within the catheter adapter.

In another aspect of the invention, an activator attachment includes an activator attachment body and a probe member of the activator attachment body. The attachment activator body includes a distal end, a proximal end, and a lumen extending between the distal and proximal ends. The lumen has an unrestricted proximal opening. The probe member has a lumen extending through the probe member. The probe member is shaped and sized to be inserted within a proximal opening of a catheter adapter.

In another aspect of the invention, a catheter assembly system includes a catheter adapter and an activator attachment. The catheter adapter has an inner lumen extending between a proximal opening of the catheter adapter and a distal end of the catheter adapter. A septum is disposed within and selectively seals the inner lumen. A septum activator is disposed within the inner lumen at a location proximal to the septum. The septum activator is configured to advance distally through a slit in the septum. The activator attachment has a distal end, a proximal end, and an unrestricted lumen extending therethrough. The distal end of the activator attachment has a probe member through which extends the lumen, the probe member having outer dimensions configured to fit within the proximal opening of the catheter adapter.

In yet another aspect of the invention, an activator attachment includes an activator attachment body comprising a distal end, a proximal end, and a lumen extending between these ends. The lumen has an unrestricted proximal opening.

A probe member of the activator attachment body has a lumen extending within the activator attachment body. The probe member is shaped and sized to be inserted within a proximal opening of a catheter adapter. The probe member has a length sufficiently long enough to contact a septum activator within the catheter adapter and advance the septum activator distally through the slit when the probe member is inserted into the proximal opening of the catheter adapter. An extension member extends distally from a distal end surface of the probe member. The extension member is shaped and sized to fit within a distal opening of an inner lumen of the septum activator. An interlocking feature is disposed on an outer surface of the extension member, the interlocking feature of the extension member being configured to interlock with an interlocking mate feature of the septum activator.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

FIG. 8 is a cross-section view of another activator attachment and catheter adapter, according to some embodiments.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the Figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
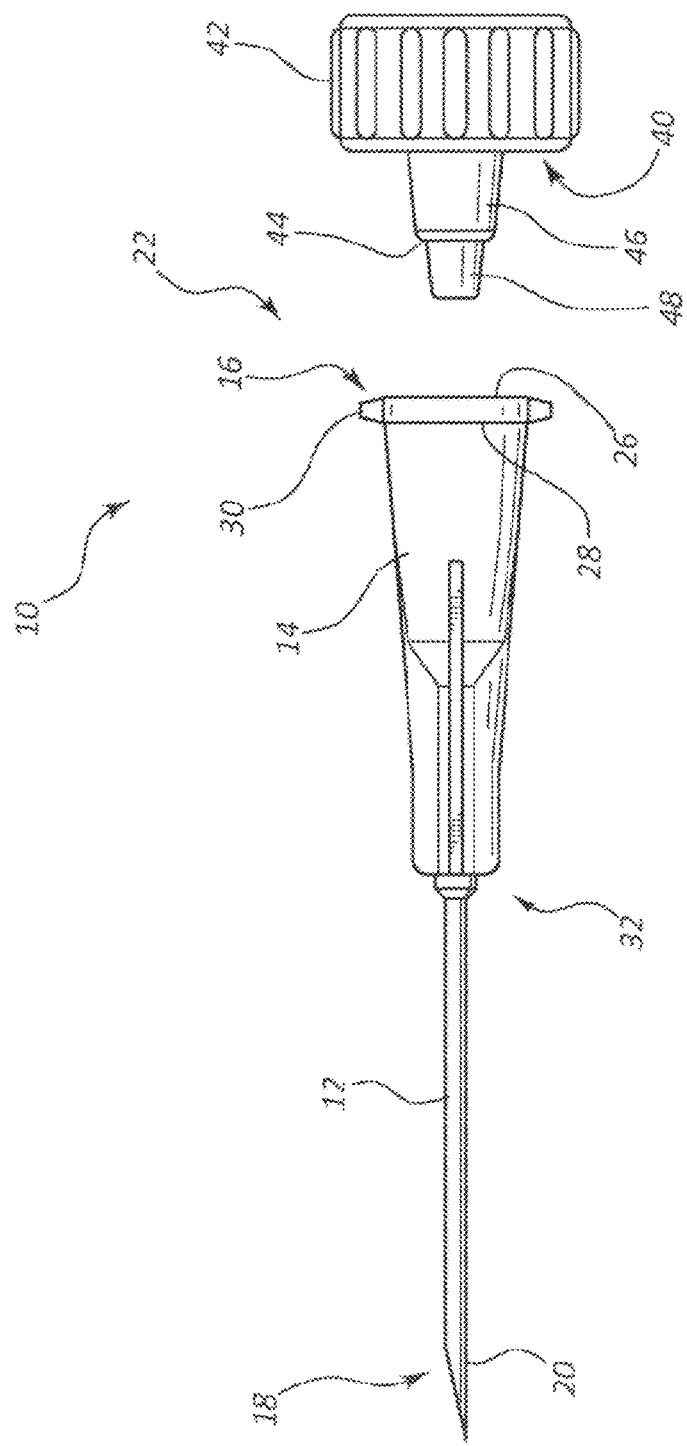
FIG. 1 is a perspective view of an embodiment of a catheter assembly and an activator attachment, according to some embodiments.

Referring now to FIG. 1, a catheter assembly 10 and an activator attachment 40 are illustrated. The catheter assembly 10 generally includes a catheter 12 coupled to a distal end 32 of a catheter adapter 14. The catheter assembly 10 can be referred to as a blood control catheter assembly when it includes a blood control valve therein. The catheter 12 and the catheter adapter 14 are integrally coupled such that an internal lumen 16 of the catheter adapter 14 is in fluid communication with a lumen 18 of the catheter 12. The catheter 12 generally comprises a biocompatible material having sufficient rigidity to withstand pressures associated with insertion of the catheter into a patient. A tip portion 20 of the catheter can be generally configured to include a beveled cutting surface. The beveled cutting surface can be utilized to provide an opening in a patient to permit insertion of the catheter 12 into the vascular system of the patient.

One of skill in the art will appreciate that the features of the present invention may be incorporated for use with an over-the-needle catheter assembly, which can include a catheter 12 with a tapered end instead of a beveled cutting surface. For example, one of skill in the art will appreciate that a flexible or semi-flexible polymer catheter may be used in combination with a rigid introducer needle to enable insertion of the catheter into a patient. One of skill in the art will further appreciate that surgically implanted catheters or other catheter types may also be used.

Once inserted into a patient, the catheter 12 and catheter adapter 14 provide a fluid conduit to facilitate delivery of a fluid to and/or retrieval of a fluid from a patient, as required by a desired infusion procedure. Thus, in some embodiments the material of the catheter 12 and the catheter adapter 14 are selected to be compatible with bio-fluids and medicaments commonly used in infusion procedures. Additionally, in some embodiments a portion of the catheter 12 and/or catheter adapter 14 is configured for use in conjunction with a section of intravenous tubing to further facilitate delivery of a fluid to or removal of a fluid from a patient through an opening 26 in the proximal end 22 of the catheter adapter 14.

In some embodiments, a proximal end 22 of the catheter adapter 14 includes a flange 28. The flange 28 provides a positive surface that may be configured to connect to intravenous tubing or an activator attachment 40 to the catheter assembly 10. In some embodiments, the flange 28 includes a set of threads 30. The threads 30 are generally provided and configured to compatibly receive a complementary set of threads of a connector portion 42 of the activator attachment 40. The threads 30 can be luer threads and form a luer port. A connector portion 42 of the activator attachment 40 is generally coupled to the proximal end 22 of the catheter adapter 14 in a fluid-tight manner. In some embodiments, an inner portion of the activator attachment 40 extends outwardly to provide a probe member 46.

In some embodiments, the proximal end 22 to the catheter adapter 14 includes a female luer connector having a female luer taper and/or female luer lock threads. The female luer taper can be disposed at least in part within the proximal portion of the inner surface 24 of the catheter adapter 14. Additionally, the flange 28 and/or threads 30 previously mentioned can comprise the female luer lock threads. The female luer connector can thus be configured to connect to a male luer lock or a male luer slip. Each of these components can be sized and configured in conformity with at least some of the International Standards Organization (ISO) standards for female and male luer connections under current or future standards. Accordingly, the proximal end 22 to the catheter adapter 14 can thus be configured to connect to a male luer lock or a male luer slip of an activator attachment 40, IV line, luer access connector, needle hub, vent plug, or other known or future developed IV device.

Figure 4:
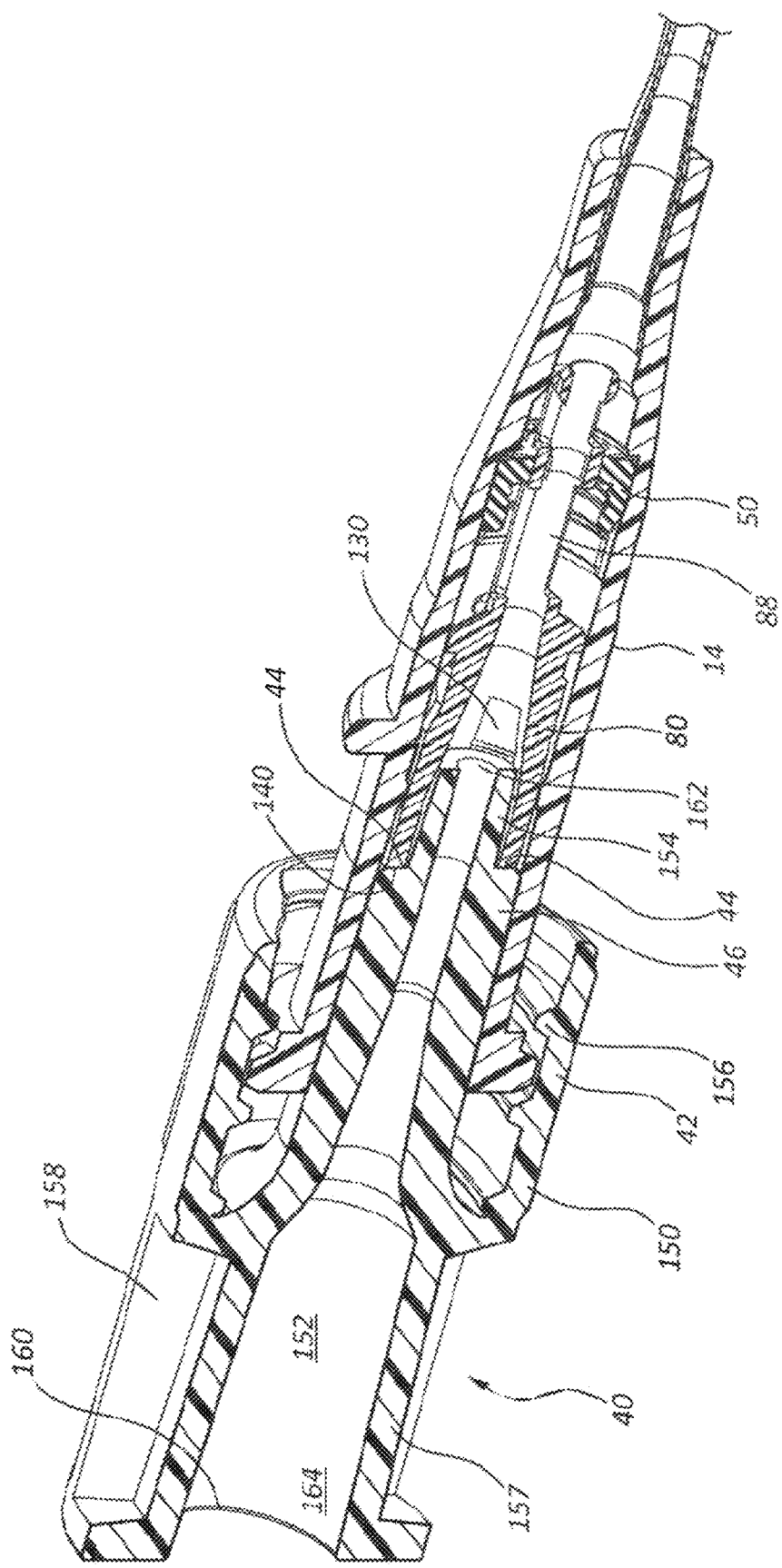
FIG. 4 is a cross-section view of a catheter assembly following activation by an activator attachment, according to some embodiments.
Figure 5:
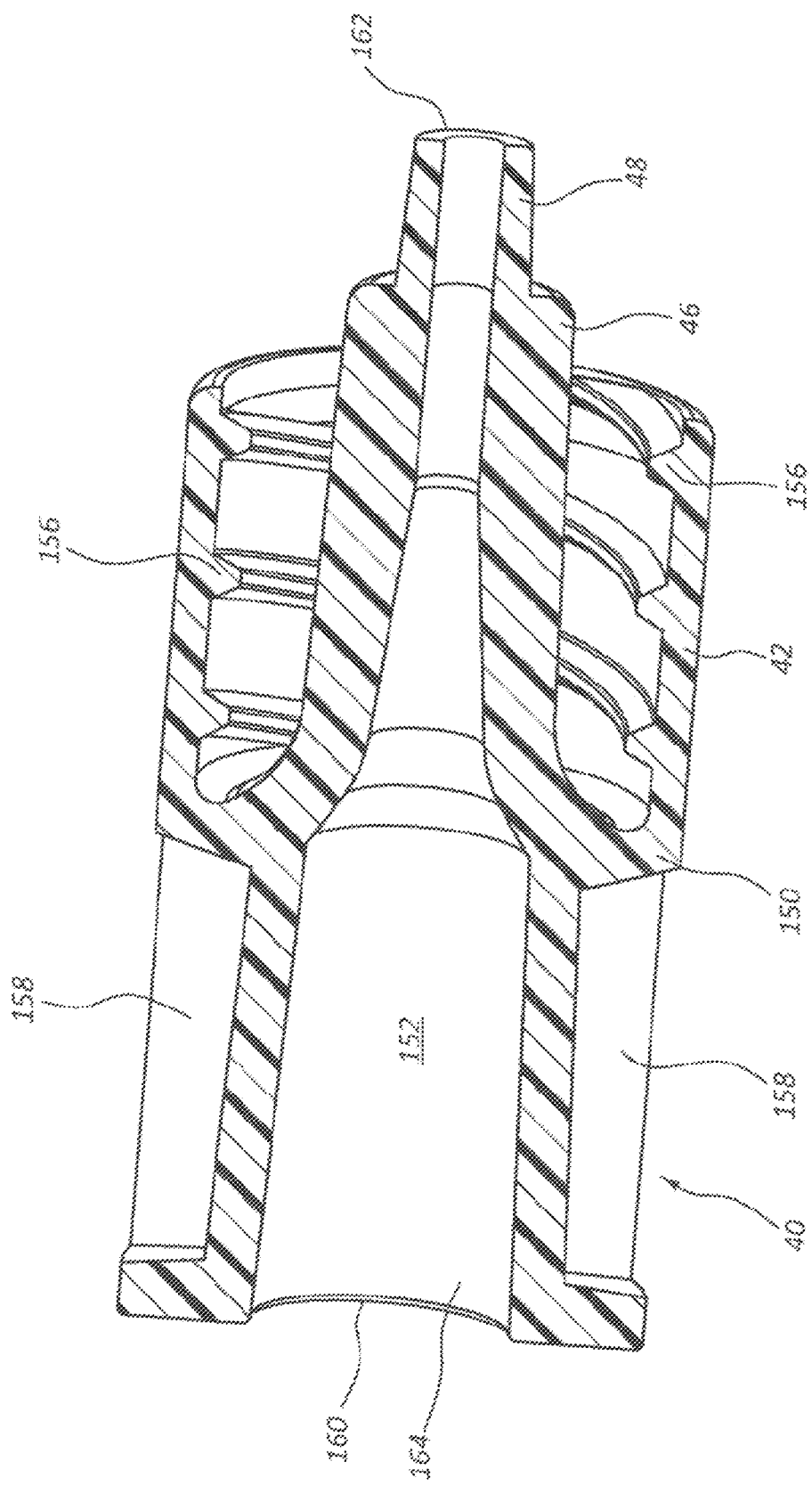
FIG. 5 is a cross-section view of the activator attachment of FIG. 4, according to some embodiments.

The probe member 46 of the activator attachment 40 can be generally configured to compatibly insert within the opening 26 in the proximal end 22 of the catheter adapter 14. The probe member 46 can thus be shaped and sized to fit within the proximal end 22 of the catheter adapter 14. The probe member 46 can be tapered so that the probe member 46 can form an increasingly tight press fitting with the opening 26 and the lumen 16 of the catheter adapter 14 as the probe member 46 is advanced deeper into the catheter adapter 14. Specifically, the probe member 46 can include a male luer taper, as previously mentioned. As such, the activator attachment 40 compatibly inserted into a female luer within the proximal end 22 of the catheter adapter 14. As shown, the probe member 46 can include an extension member 48 connected to a distal end surface 44 of the probe member 46. The extension member 48 can be inserted into the interior of a septum activator, as shown in FIGS. 4 and 5 and described with reference to those Figures.

Figure 3:
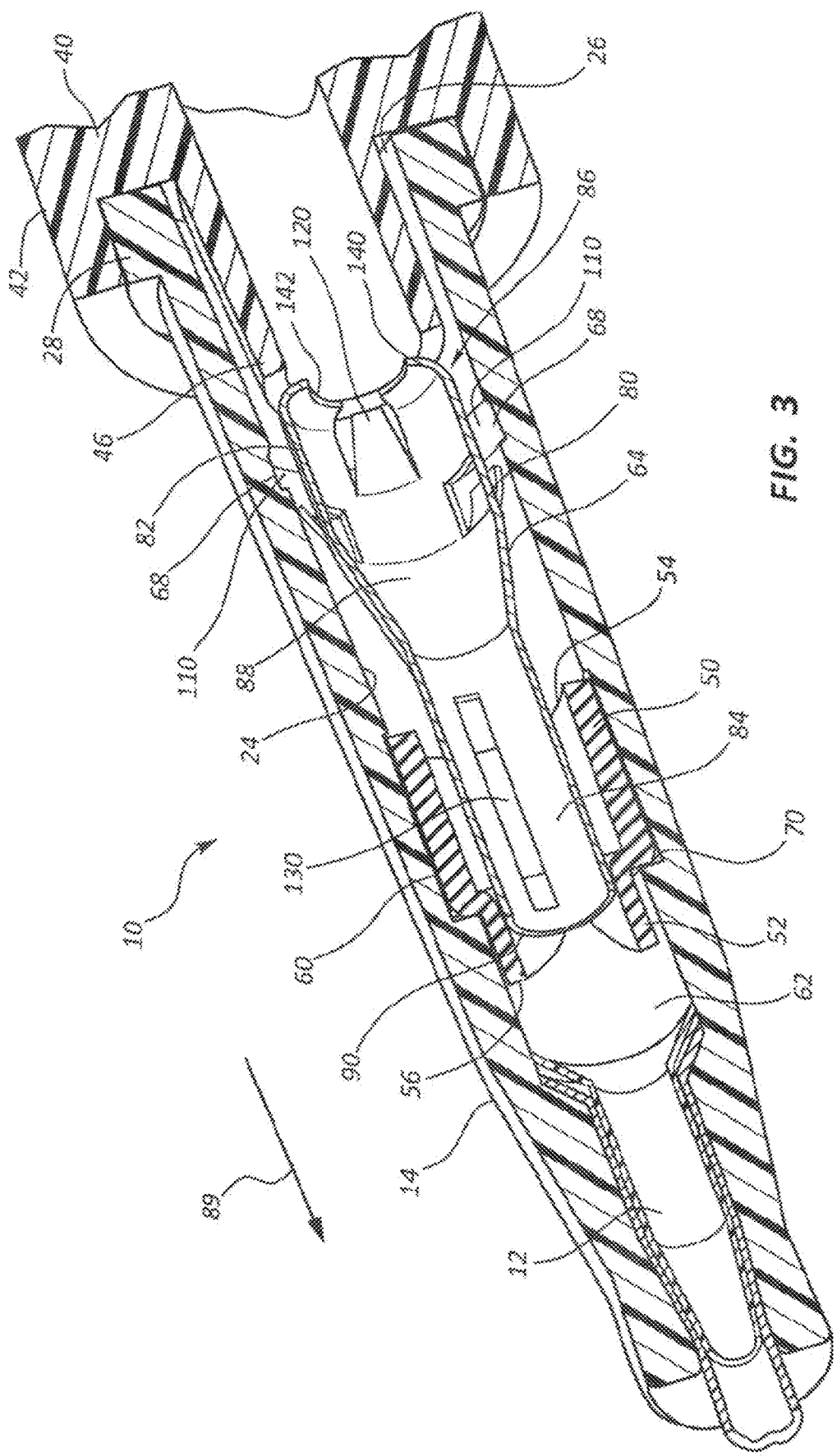
FIG. 3 is a cross-section view of the catheter assembly of FIG. 2 following activation, according to some embodiments.

Following insertion of the probe member 46 into the opening 26, the connector portion 42 of the activator attachment 40 can be rotated to interlock the connector portion 42 and the flange 28 and/or threads 30. In some embodiments, the connector portion 42 forms a collar about the probe member 46, as shown in FIG. 3. The collar can fit over the flange 28 of the catheter adapter 14 as the probe member 46 is inserted into the lumen 16 of the catheter adapter 14. Specifically, the collar can be a luer lock collar that include luer threads (not shown) or luer slip collar that does not include any threads. The probe member 46 can extend outwardly past the end of the connector portion 42.

During the process of interlocking the connector portion 42 and the flange 28, the probe member 46 is advanced into the lumen 16 of the catheter adapter 14 to an inserted position, as shown in FIG. 3. The probe member 46 [42] can be shaped and sized so that in the inserted position the probe member 46 activates a blood control valve (not shown) within the catheter assembly 10 to enable flow of fluid through the catheter 12 and the catheter adapter 14.

Figure 2:
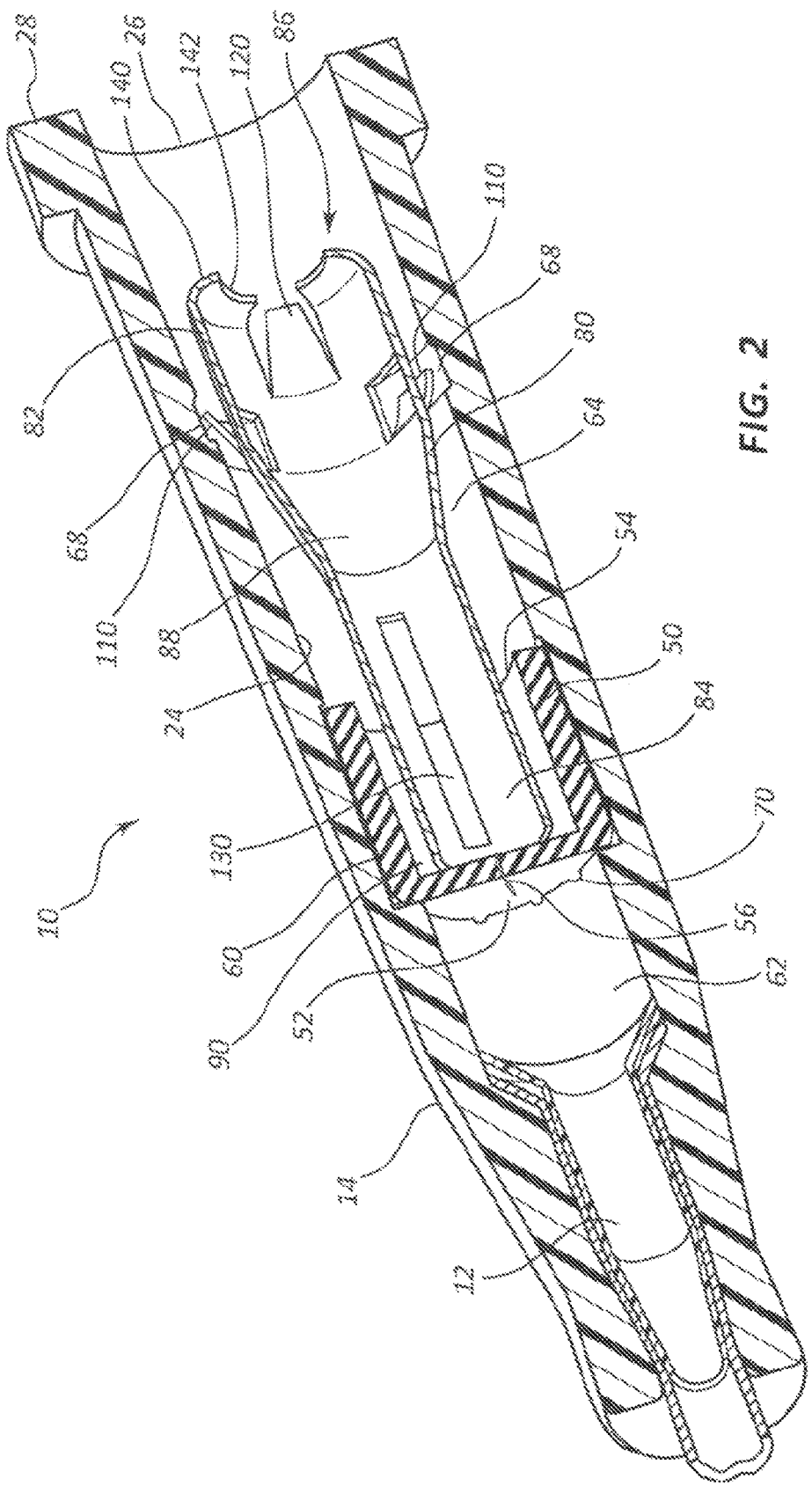
FIG. 2 is a cross-section view of a catheter assembly having a blood control valve prior to activation, according to some embodiments.

Referring now to FIG. 2, a cross-sectional view of an embodiment of a catheter assembly 10 is shown prior to activation of a septum 50 via a septum activator 80. The catheter assembly 10 includes an internal blood control valve that can be opened by the insertion of a male luer or other object into the proximal opening 26 of the catheter adapter 14. The catheter assembly 10 can include a blood control valve, which generally includes at least a septum 50 and a septum activator 80, which are disposed within the inner lumen of the catheter adapter 14.

In some embodiments, the septum 50 is positioned within the inner lumen 16 of the catheter adapter 14. The septum 50 generally comprises a flexible or semi-flexible polymer plug having an outer diameter that is configured to compatibly seat within a groove or channel 60 formed on an inner surface 24 of the catheter adapter 14. In some embodiments, the septum 50 is barrel shaped having a barrier surface 52 comprising a distal end of the septum 50 and further having an opening 54 comprising a proximal end of the septum 50. When positioned within the channel 60, the barrier surface 52 of the septum 50 divides the inner lumen 16 of the catheter adapter 14 into a forward fluid chamber 62 and a rearward fluid chamber 64. Thus, the presence of the septum 50 can control and/or limit passage of fluid between the forward and rearward fluid chambers 62 and 64. Specifically, a chosen configuration of the barrier surface 52 of the septum 50 largely determines the ability of a fluid to flow through the inner lumen 16 of the catheter adapter 14.

For example, in some embodiments the barrier surface 52 of the septum 50 is configured to include a slit 56. The slit 56 is configured to provide selective access or flow of a fluid through the barrier surface 52. In some embodiments, the slit 56 is configured to remain in a closed, fluid-tight position until activated or opened by advancing a septum activator 80 through the slit 56 in a distal direction 89. In some embodiments, the barrier surface 52 comprises one slit 56. In other embodiments, the barrier surface 52 is modified to include multiple slits 56, such as two, three, or more than three slits 56.

In some embodiments, catheter assembly 10 further comprises and introducer needle (not shown) to assist a user in accessing the patient's vein during the catheterization process. The slit 56 permits passage of the introducer needle through septum 50, thereby enabling a sharpened tip of the introducer needle to extend distally beyond the tip portion 20 of the catheter 12. Following the catheterization procedure, the introducer needle can be removed from the catheter assembly 10 and be safely disposed.

In some embodiments, the introducer needle is coated with a significant amount of silicone or similar fluid, such as fluorosilicone. The purpose of the coating fluid can be threefold. Firstly, the coating fluid can act as a lubricant between the outer surface of the introducer needle and the interfacing surfaces of slit 56. Thus, upon withdrawal of the introducer needle from the septum 50, the coating fluid prevents undesirable adhesion between the outer surface of the introducer needle and the interfacing surfaces of slit 56. Secondly, excess coating fluid accumulates within slit 56 thereby assisting in sealing the septum 50 to prevent blood from flowing back through the septum following removal of the introducer needle. Excess coating fluid accumulates within slit 56 as introducer needle is removed from catheter assembly 10. In particular, when the introducer needle is being withdrawn through septum 50, the interfacing surfaces of slit 56 act to wipe the coating fluid from the outer surface of the introducer needle thereby displacing the coating fluid into slit 56. Thirdly, the coating fluid acts as a lubricant to prevent undesirable adhesion between opposing surfaces of slit 56.

The coating fluid may include any biocompatible lubricant. In some embodiments, the coating fluid comprises a lubricant such as a non-wetting lubricant that is applied to an interface between the introducer needle and the slit 56 to further eliminate possible leakage of fluid and/or air. A non-wetting lubricant may also be beneficial to prevent tearing or other damage to the slit that may occur when the needle is removed from the catheter assembly following catheterization. A non-wetting lubricant may also facilitate proper realignment of the opposing surfaces of slit 56 following removal of the introducer needle. Non-limiting examples of a non-wetting lubricant include known TEFLON™ based non-wetting materials such as Endura, from ENDURA® Coating Co.; A20, E-20, 1000-S20, FEP Green, PTFE and X-40 from TIODIZE®; Cammie 2000 from AE Yale; 21845 from Ladd Research; MS 122-22, MS 122DF, MS-143DF, MS-122V MS-122VM, MS143V, MS-136W, MS-145W, U0316A2, U0316B2, MS-123, MS-125, MS-322 and MS-324 from Miller-Stepheson; and 633T2 from Otto Bock can also be used. Various non-TEFLON™ based non-wetting lubricant type materials include Dylyn, from ART; Nyebar, Diamonex, NiLAD, TIDLN, Kiss-Cote, Titanium oxide; Fluocad Fluorochemical Coating FC-722, from 3M; Permacote from Dupont; Plasma Tech 1633 from Plasma Tech, Inc.; and silicone sprays.

For some infusion therapy techniques, it may be desirable to permit a controlled flow of fluid through the septum 50 prior to activating the septum 50 with the septum activator 80. Thus, in some embodiments the slit 56 further comprises a leak orifice (not shown) positioned in the barrier surface 52. The leak orifice can be an open hole having dimensions calculated to permit controlled flow of liquid or air between the forward and rearward chambers 62 and 64. In some embodiments, the barrier surface 52 is modified to include a single leak orifice. In other embodiments, the barrier surface 52 is configured to include multiple leak orifices. Still, in other embodiments the barrier surface 52 does not include a slit 56, but rather includes at least one leak orifice. For these embodiments, the septum 50 generally comprises an elastic material such that when the septum activator 80 is advanced in a distal direction 89, a leading edge of the septum activator 80 contacts the barrier surface 52 and stretches the leak orifice to provide an opening that is sufficiently large to permit increased flow of air and/or fluid through the septum 50.

The groove or channel 60 into which the septum is seated comprises a recessed portion of the inner surface 24 of the catheter adapter 14. The outer diameter of the septum 50 is generally configured to compatibly and securely seat within the channel 60. For example, in some embodiments the outer diameter of the septum 50 is selected to be both slightly smaller than the diameter of the channel 60 and slightly larger than the diameter of the inner lumen 16. As such, the septum 50 is retained within the channel 60 during use of the catheter assembly 10.

For some infusion therapy techniques, air flow between the forward and rearward chambers 62 and 64 may be desirable. For example, for those embodiments comprising a septum 50 having a fluid-tight slit 56, passage of air from the forward chamber 62 to the rearward chamber 64 is prevented by the septum 50 prior to opening or activating the septum 50 via the septum activator 80, as previously discussed. Thus, when the catheter 12 of the catheter assembly 10 is inserted into the vascular system of a patient, a positive pressure develops within the forward chamber 62 thereby preventing a desired flashback of the patient's blood into the catheter adapter 14. An observable flashback is generally desirable to confirm accurate placement of the catheter tip 20 within the vein of the patient. Thus, some embodiments of the present invention include features or elements to enable airflow between the forward chamber 62 and the rearward chamber 64, without requiring activation of the septum 50 with the septum activator 80. As such, some embodiments of the present invention provide an observable flashback, as generally desired for infusion procedures.

For example, in some embodiments the barrier surface 52 of the septum 50 is modified to include leak orifice, as previously discussed. In other embodiments, a plurality of air vent channels 70 is interposed between the septum 50 and the inner surface 24 of the catheter adapter 14. The air vent channels 70 relieve the positive pressure within the forward chamber 62 by providing an access for air to bypass the septum 50 into the rearward chamber 64. In some embodiments, the air vent channels 70 are constructed by removing portions of the channel 60 surface, resulting in a plurality of generally parallel grooves.

In addition to permitting airflow between the forward and rearward chambers 62 and 64, the vent channels 70 may be configured to permit fluid to flow through the catheter adapter 14 prior to activating or opening the slit 56 with the septum activator 80. In some embodiments, the rate at which air and/or fluid flows between the forward and rearward chambers 62 and 64 is adjusted by manufacturing the catheter adapter 14 to include a greater or lesser number of vent channels 70. In other embodiments, the rate at which air and/or fluid flows between the forward and rearward chambers 62 and 64 is adjusted by manufacturing the catheter adapter 14 to include vent channels 70 having a greater or lesser cross-sectioned area. Thus, in some embodiments the rate at which air and/or fluid flows between the forward and rearward chambers 62 and 64 is increased by manufacturing a catheter adapter 14 having either an increased number of vent channels 70, or vent channels 70 having a greater cross-sectioned area. Conversely, in other embodiments the rate at which air and/or fluid flows between the forward and rearward chambers 62 and 64 is decreased by manufacturing a catheter adapter 14 having either a decreased number of vent channels 70, or vent channels 70 having a lesser cross-sectioned area.

With continued reference to FIG. 2, as mentioned, the blood control valve includes a septum activator 80 that can activate the septum 50. The septum activator 80 can comprise a probe-like structure that is primarily housed in the rearward chamber 64 of the catheter adapter 14. The septum activator 80 generally comprises a tubular body 82 having a distal end 84 and a proximal end 86. The tubular body 82 comprises a rigid or semi-rigid material, such as a plastic or metallic material. The tubular body 82 further comprises an inner lumen 88 for facilitating flow of a fluid and/or liquid through the septum activator 80.

The distal end 84 of the tubular body 82 is configured to compatibly insert within the opening 54 of the septum 50. The distal end 84 further includes a probing surface 90 that extends through the opening 54 of the septum 50 to a position proximal to the barrier surface 52 of the septum 50, as shown. The probing surface 90 is advanced through the slit 56, or through the leak orifice as the septum activator 80 is advanced through the catheter adapter 14 in a distal direction 89. Advancement of the septum activator 80 through the catheter adapter 14 will be discussed in detail below, in connection with FIG. 3.

In some embodiments of the septum activator 80, the distal end 84 of the tubular body 82 comprises a first diameter that is less than a second diameter of the proximal end 86. The narrower distal end 84 is configured to compatibly insert within the slit 56 of the septum 50, while the wider proximal end 86 is configured to compatibly seat within the rearward chamber 64 of the catheter adapter 14. In some embodiments, the septum activator 80 further includes a tapered middle section joining the distal 84 and proximal 86 ends. The entirety of the septum activator 80 can comprise a single-piece, unitary structure.

In some embodiments, the proximal end 86 of the septum activator 80 further includes a retention spring 110. The retention spring 110 generally comprises an outwardly biased portion of the tubular body 82 configured to compatibly engage a retention groove 68 of the catheter adapter 14, as shown in FIG. 2. The interaction between the retention spring 110 and the groove 68 can limit the lateral movement of the septum activator 80 within the lumen 16 of the catheter adapter 14. Thus, the width of the retention groove 68 determines or limits the distance of travel for the septum activator 80 within the catheter adapter 14. Additionally, the interaction between retention spring 110 and the groove 68 can prevent removal of the septum activator 80 from the catheter adapter 14. In some embodiments, the septum activator 80 comprises a plurality of retention springs 110, while in other embodiments the septum activator 80 comprises only a single retention spring 110.

In some embodiments, the septum activator 80 further comprises features for directing or diverting fluid flow around and/or through the septum activator 80. Flow diversion may be important to prevent the stagnation or coagulation of fluids within dead zones within the septum activator 80 and/or the lumen 16 of the catheter adapter 14. Additionally, stagnation of fluid flow through the catheter assembly 10 may result in a buildup of undesirable concentrations of medicaments within the catheter adapter 14 and/or the septum activator 80. Undesirable high concentrations may result in ineffective treatment causing serious side effects, including death. Thus, in some embodiments the septum activator 80 is modified to include flow deflectors 120 and flow diversion channels 130 to provide a flushable catheter assembly 10 system.

The flow deflectors 120 can generally comprise inwardly and outwardly angled portions of the outer surface of the septum activator 80. The flow deflectors 120 can be positioned to protrude into a flow path through the catheter adapter 14. Thus, as the fluid contacts the flow deflectors 120 the path of the fluid flow is disturbed. This disturbance results in redirecting the fluid flow both through the inner lumen 88 of the septum activator 80, and between the outer surface of the septum activator 80 and the inner surface 24 of the catheter adapter 14. In some embodiment, the retention spring 110 also serves as a flow deflector 120.

A flow diversion channel 130 can be provided to permit exchange of fluid between the lumen of the catheter adapter 14 and the inner lumen 88 of the septum activator 80. Thus, the flow diversion channel 130 prevents stagnation and/or clotting of fluid between the inner surface 24 of the catheter adapter 14 and the outer surface of the septum activator 80. In some embodiments, the flow diversion channel 130 comprises a window or opening in the surface of the tubular body 82. In other embodiments, the flow diversion channel 130 further comprises a flap or angled surface to further direct fluid to flow through the channel 130.

The proximal end 86 of the septum activator 80 further includes a contact surface 140. The contact surface 140 comprises the most proximal end portion of the septum activator 80 and is positioned within the rearward chamber 64 of the catheter adapter 14 adjacent to the proximal opening 26 of the catheter adapter 14.

As shown in FIG. 2, prior to activation, the septum activator 80 is entirely positioned within the rearward fluid chamber 64 of the catheter adapter 14. Additionally, the retention springs 110 are engaged within the retention groove 68 and positioned near the proximal end of the retention groove 68. A contact surface 140 on the proximal end 86 of the septum activator 80 is positioned near the opening 26 of the catheter adapter 14. In some embodiments, a proximal opening 142 of the septum activator 80 can be in a plane generally parallel to the plane of the catheter adapter opening 26. Finally, the outwardly biased retention springs 110 can bind on the surface of the groove 68 thereby maintaining the inactivated position of the septum activator 80 within the catheter adapter 14.

Referring now to FIG. 3, a cross-sectional view of the catheter assembly 10 is shown following activation of the septum 50 via the septum activator 80. As described above, in some instances, it can be desirable to activate the septum 50 in order to permit fluid flow there through during certain medical procedures. For example, it can be desirable to activate the septum 50 via an activator attachment 40 in order to introduce a guide wire into the catheter adapter 14. It can also be desirable to activate the septum 50 using the activator attachment 40 in order to perform a blood draw through the proximal opening 26 of the catheter adapter 14.

Accordingly, upon insertion of the activator attachment 40 into the proximal opening 26 of the catheter adapter 14, the probe member 46 of the activator attachment 40 contacts the contact surface 140 of the septum activator 80. The septum activator 80 is advanced in a distal direction 89 as the activator attachment 40 is further inserted into the proximal opening 26 of the catheter adapter 14. As the activator attachment 40 is advanced further into the proximal opening 26, the probing surface 90 of the septum activator 80 passes through the slit 56 in the barrier surface 52 of septum 50. As such, the probing surface 90 of the septum activator 80 enters into the forward chamber 62 providing a fluid pathway through the septum 50. Using this open fluid path, a clinician can perform a blood draw or insert a guide wire. It will be understood, that the activator attachment 40 can be used for other procedures in addition to performing blood draws and inserting type wires.

In some embodiments, the catheter assembly 10 is configured to permit the septum activator 80 to return to a position entirely within the rearward chamber 64 following removal of the activator attachment 40 from the catheter adapter 14. Thus, when the activator attachment 40 is removed or detached from the catheter assembly 10, the fluid pathway through the septum 50 is reclosed. In some embodiments, the retention spring 110 is configured to flex inwardly upon contact between the contact surface 140 of the septum activator 80 and the probe member 46 of the activator attachment 40. When the retention spring 110 flexes inwardly, the probing surface 90 of the septum activator 80 is temporarily advanced in a distal direction 89 to bias open the slits 56, or the leak orifice. When contact between the probe member 46 and the contact surface 140 ceases, the retention spring 110 returns to its relaxed position. The relaxed position withdrawals the probing surface 90 of the septum activator 80 from the barrier surface 52 thereby permitting closure of the slits 66 and 56.

Reference will now be made to FIGS. 4 and 5, which illustrate an example of an activator attachment 40, according to some embodiments. FIG. 4 specifically illustrates an activator attachment 40 attached to a catheter assembly 10 having a blood control valve. FIG. 5 illustrates an isolated view of the activator attachment 40 of FIG. 4.

As shown, the activator attachment 40 can generally includes a distal end, a proximal end, and a lumen 152 extending between these ends. The body of the activator attachment 40 can be an integral, unitary body that can be formed as a single piece. The lumen 152 can have an unrestricted proximal lumen opening 160 through which a clinician can take a blood draw and/or introducing an object into the catheter assembly 10, such as a guide wire. The unrestricted opening can be a direct opening into the lumen 154 of the activator attachment, in which no object is present and which provides unrestricted access into the lumen 154. Furthermore, the lumen 152 can be unrestricted, such that it forms a direct an unobstructed path from the proximal lumen opening 160 to a distal lumen opening in the distal end of the activator attachment 40.

The body of the activator attachment 40 can include a probe member 46 extends outwardly. The probe member 46 can be configured to activate the blood control valve when it is attached to the proximal end 22 of the catheter adapter 14. As the activator attachment 40 activates the blood control valve, a fluid path is open between the external environment and the forward fluid chamber 62 of the catheter adapter 14. This fluid path extends from a proximal lumen opening 160 to a distal lumen opening 162 of the activator attachment 40. This fluid path permits clinicians to access the forward fluid chamber 62, the catheter 12, and the vasculature of a patient through the proximal lumen opening 160 of the activator attachment 40. Thus attached, blood draws can be performed through the activator attachment 40, and secondary catheters and guide wires for longer dwell catheters can be inserted through the activator attachment 40.

As shown in FIG. 4, the probe member 46 of the activator attachment 40 can have sufficient length to contact the contact surface 140 of the septum activator 80 to advance the septum activator 80 through the septum 50. The distal end of the probe member 46 can include an extension member 48 that is shaped and sized to enter the proximal opening 142 (shown in FIGS. 2 and 3) of the septum activator 80 when the activator attachment 40 is inserted into the proximal opening 26 of the catheter adapter 14. As shown, the probe member 46 can have a distal end surface 44 that is configured to contact the contact surface 140 of the septum activator 80 to advance the septum activator 80. The extension member 48 can extend away from the distal end surface 44 of the probe member 46. The extension member 48 has outer dimensions that approximate the inner dimensions of the proximal opening 142 of the septum activator 80. For example, an outer diameter of the extension member 48 can approximate or be smaller than the inner diameter of the proximal opening 142 of the septum activator 80.

The extension member 48 can provide various functions to the activator attachment 40. For example, the extension member 48 can direct a guide wire toward the septum 50. As shown, the extension member 48 can also be shaped and sized to cover at least a portion of one or more openings 130 within the septum activator 80 to prevent fluids or a guide wire from entering these openings 130. The extension member 48 can also align the probe member 46 against the contact surface 140 of the septum activator 80 as it is inserted into the catheter adapter 14. In some embodiments, the exterior dimensions of the extension member 48 are configured to closely approximate the dimensions of the interior of the septum activator 80 to prevent fluid flow out proximal lumen opening 142 of the septum activator 80 and/or through flow diversion channels 130 in the septum activator 80.

In some embodiments, the activator attachment 40 can be inserted into but not coupled to the catheter adapter 14. In these embodiments, the activator attachment 40 can be press fit into the catheter adapter 14. In other embodiments, such as those shown in FIGS. 4 and 5, the activator attachment 40 is connected to the catheter adapter 14. The activator attachment 40 can be connected to the catheter adapter 14 using various connecting means including, the press fit connection, a threaded connection, a latch, a snap-fit connection, and other suitable connections. As mentioned, in a specific embodiment, this connection can be between a male luer connector of the activator attachment 40 and a female luer connector of the catheter adapter 14. For instance, as shown, the activator attachment 40 can connect to the catheter adapter 14 via one or more set of male luer threads 156 that are configured to compatibly receive and couple to a complementary set of female luer threads 30 of the catheter adapter 14. To facilitate forming a secured connection the activator attachment body 150 can include grip features 158 such as ribs, a textured surface, or other suitable grip features.

As further shown in FIG. 4, the proximal lumen opening 160 of the activator attachment 144 can be larger than the distal lumen opening 162. The larger proximal lumen opening 160 can facilitate the insertion of a guide wire or other device. Accordingly, in various embodiments, the inner lumen 152 can taper inwardly between the proximal lumen opening 160 and the distal lumen opening 162. In some embodiments, the proximal portion of the lumen 152 includes a female luer taper 164.

In some embodiments, as shown in FIG. 4, the activator attachment 40 can optionally include a channel portion 157 of forms a proximal portion of the activator attachment 40, and which is proximal to the connector portion 42. The channel portion 157 can be connected directly to the probe member 46 such that the lumen 152 at the channel portion 157 connects directly into the lumen 152 extending through the probe member 46. The channel portion 157 can form an extended portion of the activator attachment 40 through which the lumen 152 extends. The portion of the lumen 152 within the channel portion 157 can have a wider cross-section (taken in a plane perpendicular to the longitudinal axis of the lumen 152) than the portions of the lumen disposed within the probe member 46. As such, medical personnel can have a larger target area into which they can insert objects into the proximal lumen opening 160 and from which they can retrieve blood through this opening.

As will be understood, the activator attachment 40 can have various shapes and sizes. In some embodiments, the length of the activator attachment 40 extending between the proximal and distal ends can be increased or decreased depending on the desired size, the size of the proximal lumen opening 160, and/or the intended use. In some embodiments, as shown in FIG. 6, the activator attachment 40 does not include a grip feature 158 nor does it extend proximally beyond the connector portion 42 of the activator attachment 40.

Figure 6:
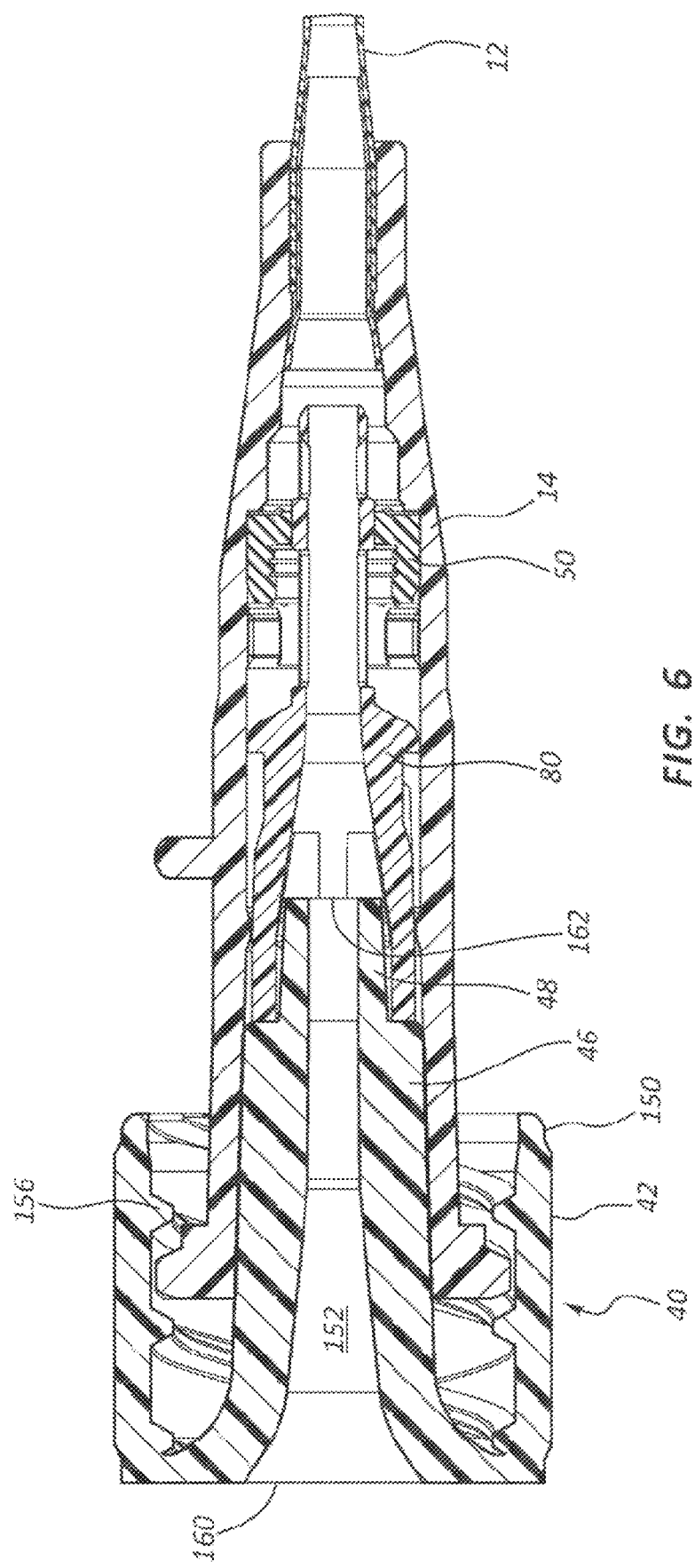
FIG. 6 is a cross-section view of a catheter assembly following activation by an activator attachment, according to some embodiments.

FIG. 6 illustrates an example of an activator attachment 40 that does not include the channel portion 157. Rather, the activator attachment 40 terminates at a proximal end of the probe member 46. At this location, the lumen 152 can open into the proximal lumen opening 160. In some embodiments, this activator attachment 40 includes only a probe member 46 that is connected to a catheter adapter 14 via a connector portion 42. The probe member 46 can be a male luer, and the connector portion 42 can be a male luer lock collar having male luer threads 156. Moreover, as shown this activator attachment 40 can include an extension member 48.

Reference will now be made to FIGS. 7A through 7E, which illustrate the use of an activator attachment 40 that has one or more interlocking features 170 on the extension member 48. The one or more interlocking features 170 can be used to interlock the extension member 48 with the septum activator 80. By interlocking the extension member 48 with the septum activator 80, the extension member 48 can be able to pull the septum activator 80 out of the septum 50 to close the blood control valve after the activator attachment 40 is done being used. The septum activator 80 can be pulled back by the activator attachment 40 through the interlocking features 170, which is connected to the septum activator 80. Thus, as the activator attachment 40 is disconnected from the catheter adapter 14, the blood control valve can be automatically close.

Figure 7A:
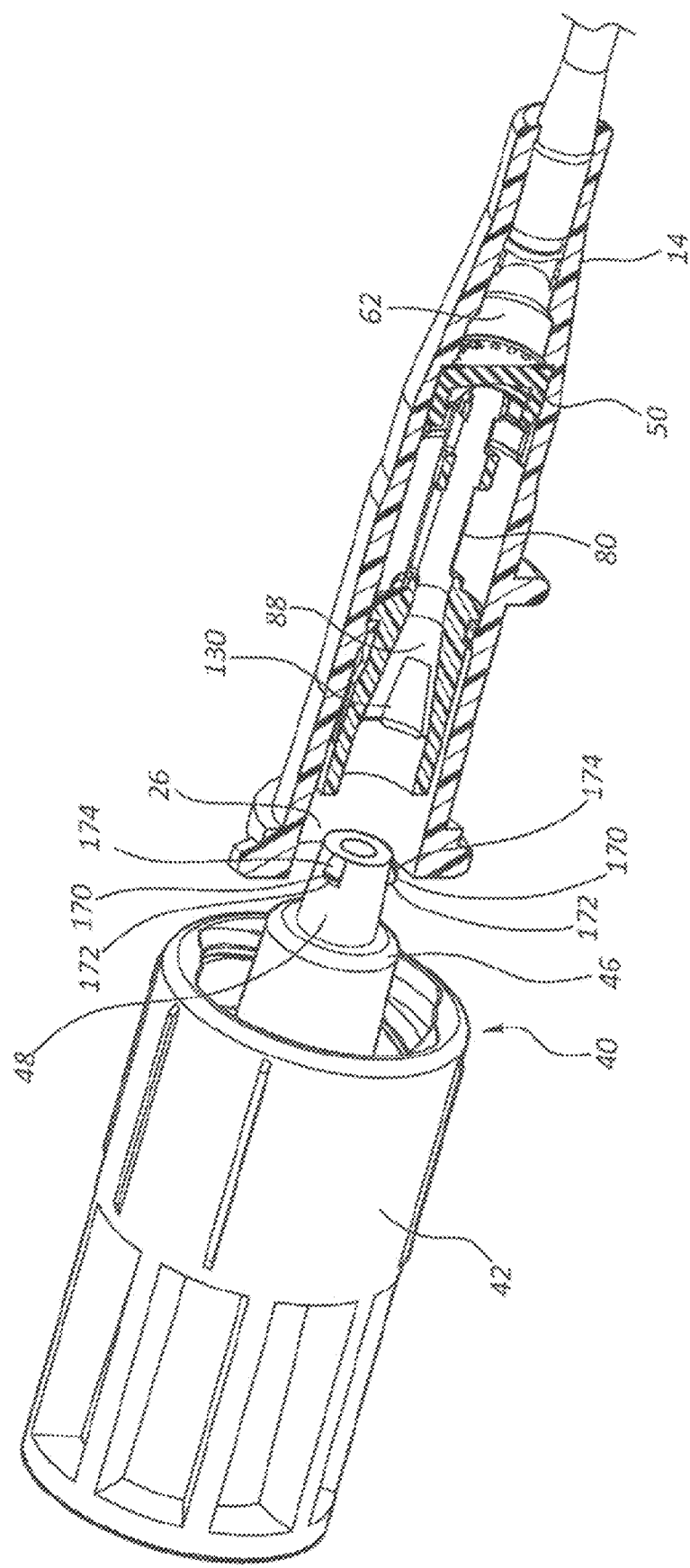
FIG. 7A is a cross-section view of another activator attachment prior to its connection with a catheter adapter, according to some embodiments.

As shown in FIG. 7A, the activator attachment 40 can include a plurality of interlocking features 170 on an outer surface of the extension member 48. For example, one, two, three, four, five, six, or more than six interlocking features 170 can be disposed on the outer surface of the extension member 48. Each interlocking feature 170 can be a protrusion that protrudes outwardly from the outer surface of the extension member 48. As shown, some interlocking features 170 can be a substantially triangular-shaped protrusion. For example, an interlocking feature 170 can include two opposing sloping surfaces 172, 174 which can combine to form a triangular-shaped protrusion. At least some of the interlocking feature 170 can be inserted into an interlock make feature of the septum activator 80 when the activator attachment 40 is attached to the catheter adapter 14. As shown, the interlock make feature can include a hole or depression within the inner lumen 88 of the septum activator. Examples of a hole include the flow diversion channels 130 in the septum activator 80. In other embodiments, the interlocking feature 170 can be a depression in the outer surface of the extension member 48, and the interlocking mate feature of the septum activator 80 can be a protrusion on the interior of the inner lumen 88 that interlocks with the depression.

Specific reference will now be made to the operations illustrated in FIG. 7A through 7E. As shown in FIG. 7A, the activator attachment 40 can be positioned near the catheter adapter 14, with the probe member 46 and the extension member 48 positioned near the proximal opening 26 of the catheter adapter 14. As the extension member 48 is advanced into the lumen 88 of the septum activator 80, the distal sloping surfaces 174 of the interlocking features 170 can accommodate gradual entry of the extension member 48 into the lumen 88. The slope of the distal sloping surface 174 and the overall height of the interlocking feature 170 can be configured such that the force required to insert the extension member 48 with the interlocking features 170 into the lumen 88 is less than the force required to advance the septum activator 80 through the septum 50. As such, the act of inserting the extension member 48 into the lumen 88 may not advance the septum activator 80 through the septum 50.

Figure 7B:
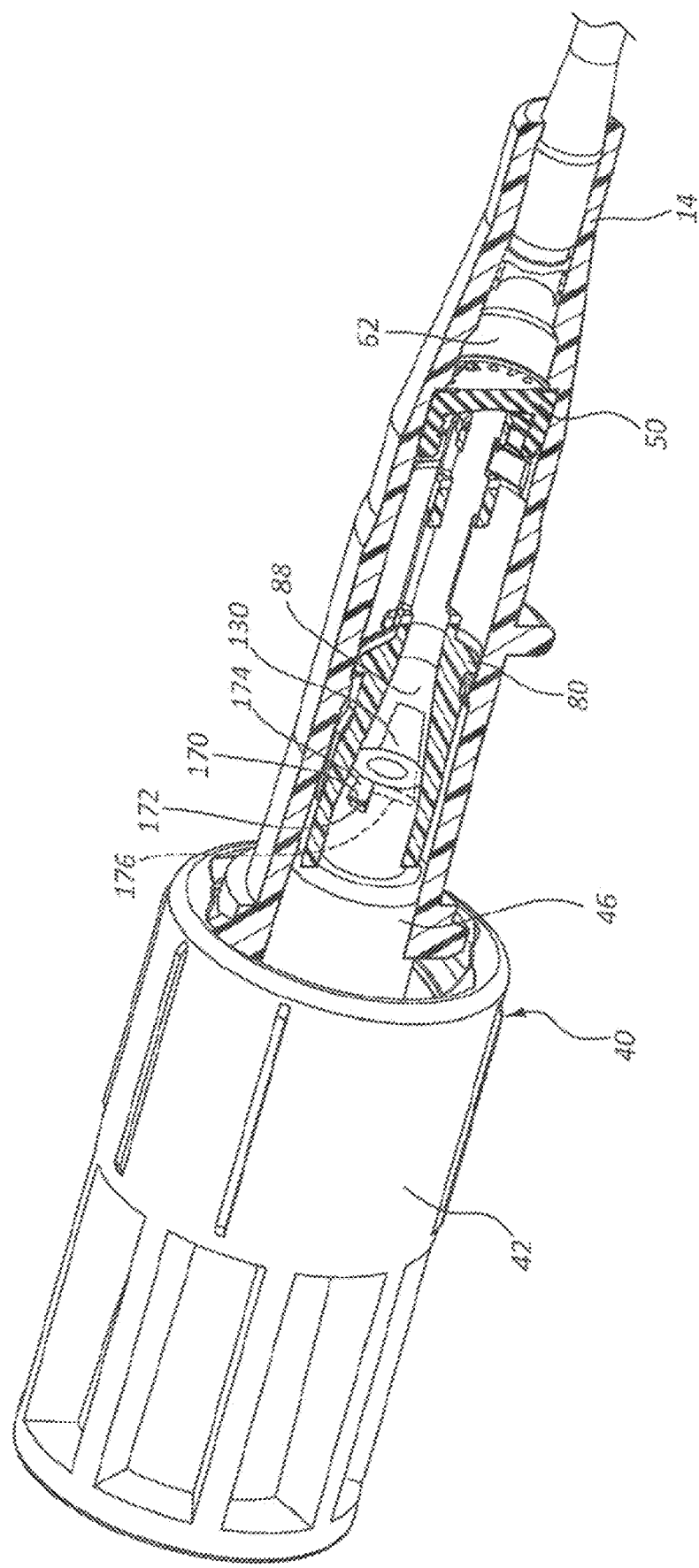
FIG. 7B is a cross-section view of the activator attachment and catheter adapter of FIG. 7A as the activator attachment is being connected to the catheter adapter, according to some embodiments.

As shown in FIG. 7B, as the activator attachment 40 is attached to the catheter adapter 14, the probe member 46 and the extension member 48 are inserted into the proximal opening 26 of the catheter adapter 14. As the extension member 48 enters into the internal lumen 88 of septum activator 80, the interlocking features 170 can interlock with the interlock mate features. For instance, as shown the triangle-shaped protrusions are inserted within the flow diversion channels 130 to interlock the probe member 46 with the septum activator 80. At this point, the activator attachment 40 may be entirely advanced or connected over the catheter adapter 14. Alternatively, at this point, the activator attachment 40 may not be entirely advanced or connected over the catheter adapter 14. For example, at this point the activator attachment 40 can have been advanced into the catheter adapter 14 to the point at which the male luer connection of the connector portion 42 of the activator attachment 40 contacts the female luer connection (which can include flange 28 and threads 30) of the catheter adapter 14. Further distal advancement may be possible by threading or press fitting the connector portion 42 to the catheter adapter 14.

Figure 7C:
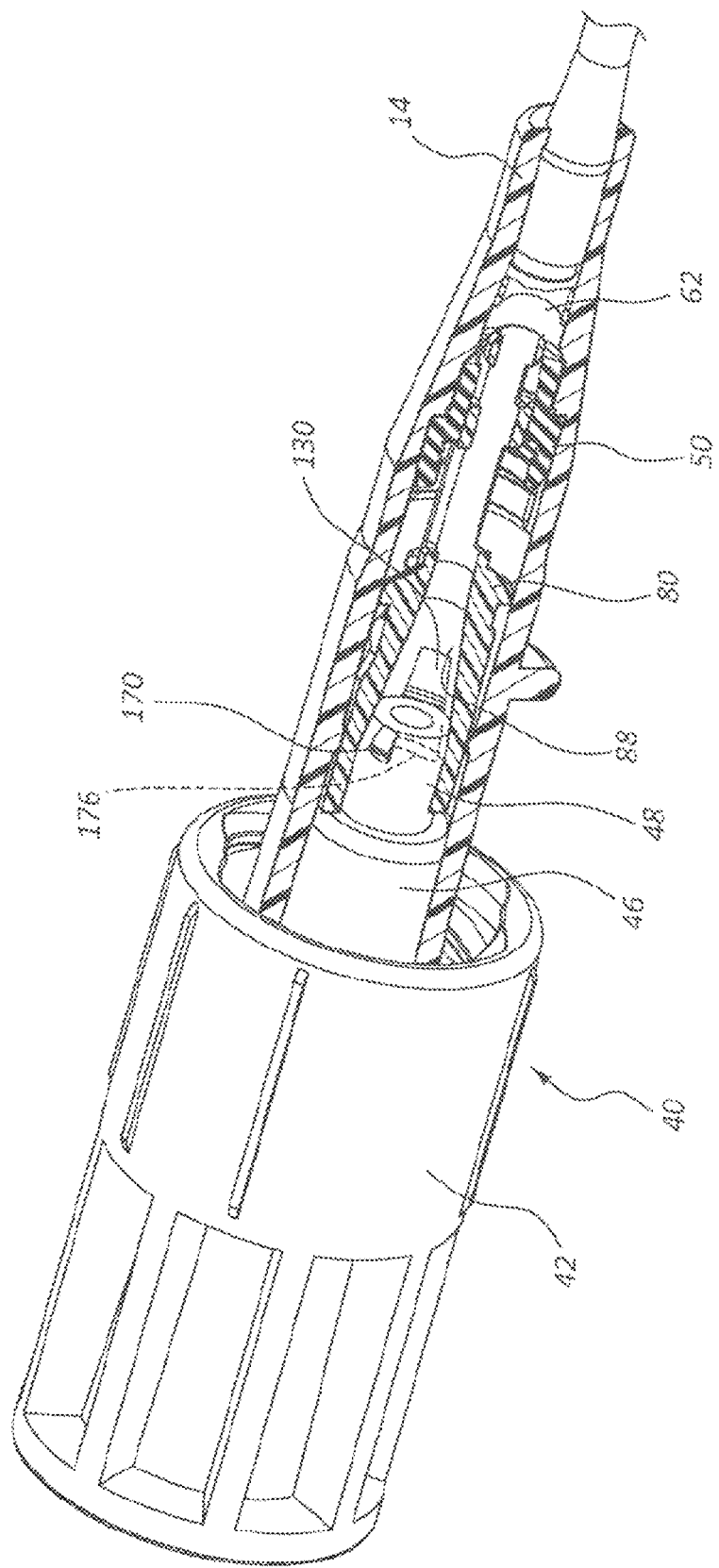
FIG. 7C is a cross-section view of the activator attachment and catheter adapter of FIGS. 7A-7B after the activator attachment is fully connected to the catheter adapter, according to some embodiments.

As shown in FIG. 7C, as the activator attachment 40 is advanced farther over the catheter adapter 14, the probe member 46 of the activator attachment 40 pushes on the contact surface 140 of the septum activator 80, advancing the septum activator 80 through the septum 50. This action can open a fluid channel through the activator attachment 40 into the distal fluid chamber 62 of the catheter adapter 14. Continuing the previous example, this distal movement of the activator attachment 40 can be made at least in part as the male luer connection of the connector portion 42 is connected to the female luer connection of the catheter adapter 14. This connection can involve a slip connection or a threaded connection, in which the male luer connection is screwed down over the female luer connection.

Figure 7D:
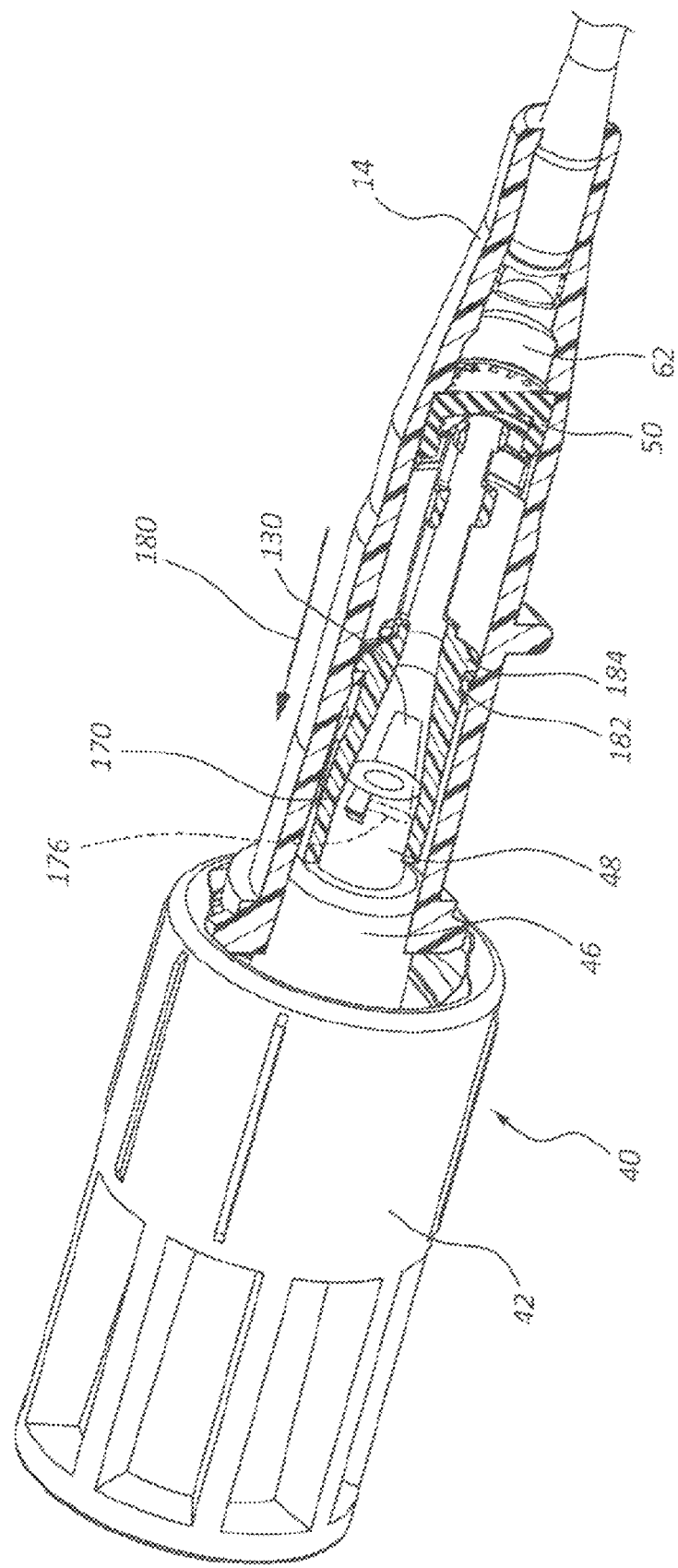
FIG. 7D is a cross-section view of the activator attachment and catheter adapter of FIGS. 7A-7C as the activator attachment is being disconnected from the catheter adapter, according to some embodiments.

As shown in FIG. 7D, the activator attachment 40 can be removed as it is withdrawn back through the septum 50 in a proximal direction 180 as the activator attachment 40 is withdrawn. As the activator attachment 40 is withdrawn, the proximal sloping surface 172 of the interlocking features 170 can contact a surface 176 of the interlock make feature (e.g., the flow diversion channels 130 to move the septum activator 80 in the proximal direction 180. As such, the activator attachment 40 can pull the septum activator 80 out of the septum 50 to close the septum 50. Accordingly, in some embodiments, the slope or other characteristic of the proximal sloping surface 172 and the overall height of the interlocking feature 170 can be configured such that the force required to withdraw the extension member 48 with the interlocking features 170 out of the lumen 88 of the septum activator 80 is greater than the force required to withdraw the septum activator 80 from within the septum 50. As such, the initial movement of the activator attachment 40 in the proximal direction 180 does not withdraw the extension member 48 from the lumen 88 of the septum activator 80.

As further shown in FIG. 7D, inner surface 24 of the catheter adapter 14 can include a retention member 182, such as the illustrated annular protrusion. The retention member 182 can assist to retain the septum activator 80 within the lumen 16 of the catheter adapter 14 and limit the proximal movement of the septum activator 80 beyond a certain point. Moreover, as shown, the septum activator 80 can include a retention feature 184 that catches or otherwise contact retention member 182 to prevent any further proximal movement of the septum activator 80. In other embodiments, the retention member is a depression formed within the inner surface 24 of the catheter adapter 14. For example, as previously described with reference to FIG. 2, the catheter adapter 14 can include a retention groove 68 that limits lateral movement of the septum activator 80. Similarly, as previously described retention feature 184 of the septum activator 80 can be a retention spring 110, as also described with reference to FIG. 2. Additionally, other types of retention members in retention features 184 are contemplated.

The retention member 182 and/or retention feature 184 can stop the proximal movement of the septum activator 80 at a certain point. This point can be at a location in which the septum activator 80 is fully withdrawn from the septum 50. When the septum activator 80 is withdrawn from the septum 50 this point, the septum can return to its closed position, closing the blood control valve.

Figure 7E:
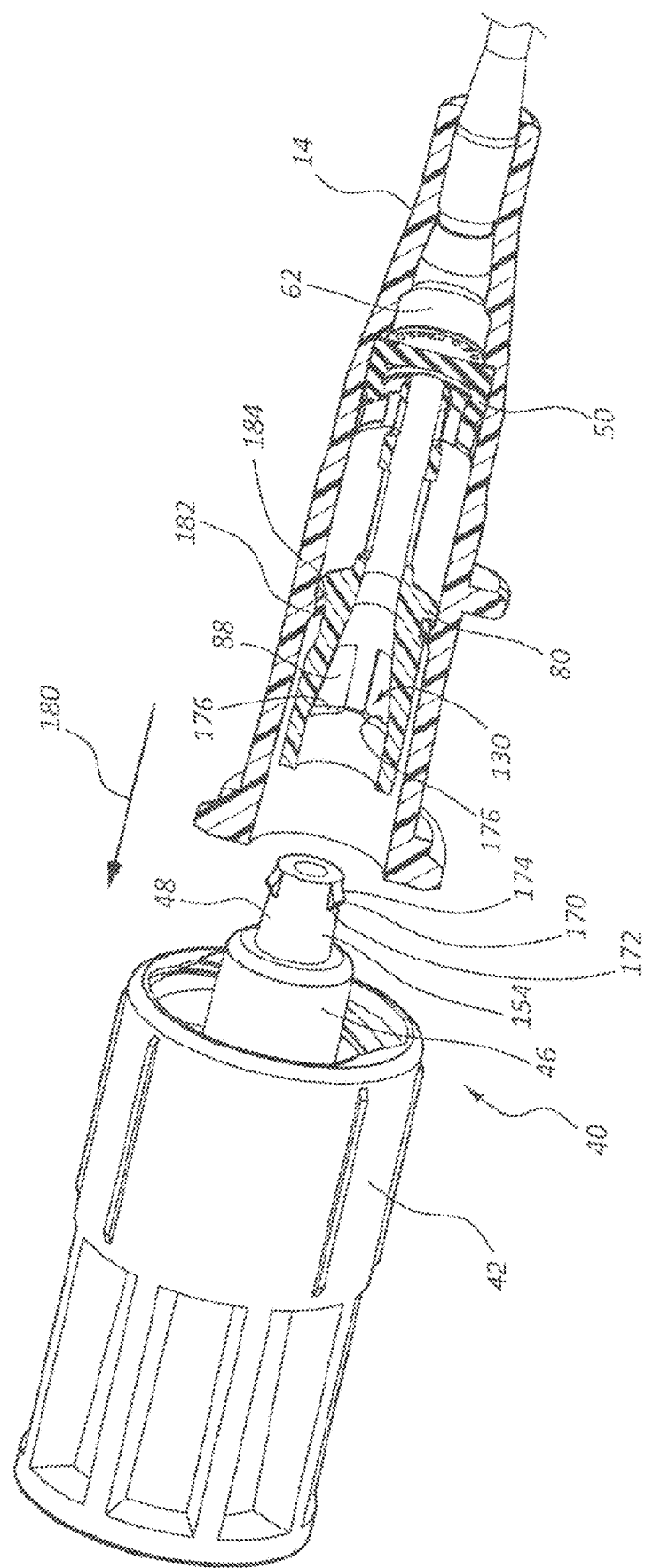
FIG. 7E is a cross-section view of the activator attachment and catheter adapter of FIGS. 7A-7D after the activator attachment is fully disconnected from the catheter adapter, according to some embodiments.

As shown in FIG. 7E, the activator attachment 40 is withdrawn farther in the proximal direction 180 at which point it disconnects from the catheter adapter 14 and septum activator 80. In some embodiments, this includes unscrewing the male luer connector of the activator attachment 40 from the female luer connector of the catheter adapter 14.

In some embodiments, during activator attachment withdrawal, the applied force on the activator attachment 40 can overcome the force required to withdraw the extension member 48 and locking interlocking features 170 out of the lumen 88 of the septum activator 80. Moreover, the proximal sloping surface 172 can be configured such that the force required to withdraw the extension member 48 out of the lumen 88 of the septum activator 80 is less than the force required to physically break either the extension member 48 or the septum activator 80. As such, after the septum activator 80 is stopped by the retention member and/or retention feature 184, additional force on the activator attachment 40 will cause the activator attachment 40 to release from the septum activator 80. Additionally, the force required to release activator attachment 40 from the septum activator 80 can be such that it can be done by a single-user using a single hand and with only a minimal, reasonable amount of force.

FIG. 8 illustrates another example of an extension member 48 configured to interlock with a septum activator 80. As shown, the outer dimensions of the outer surface 190 of the extension member 48 can be configured so that they form a friction lock with the inner surface 192 of the inner lumen 88 of the septum activator 80. The outer dimensions of the outer surface 190 and the inner dimensions of the inner surface 192 of the inner lumen 88 of the septum activator 80 can be configured so that the force required to insert the extension member 48 into the inner lumen 88, advance the septum activator, withdraw the septum activator, and withdraw the extension member 48 from the inner lumen 88 is approximately the same as the same relative forces described with reference to FIGS. 7A through 7E.

Figure 9A:
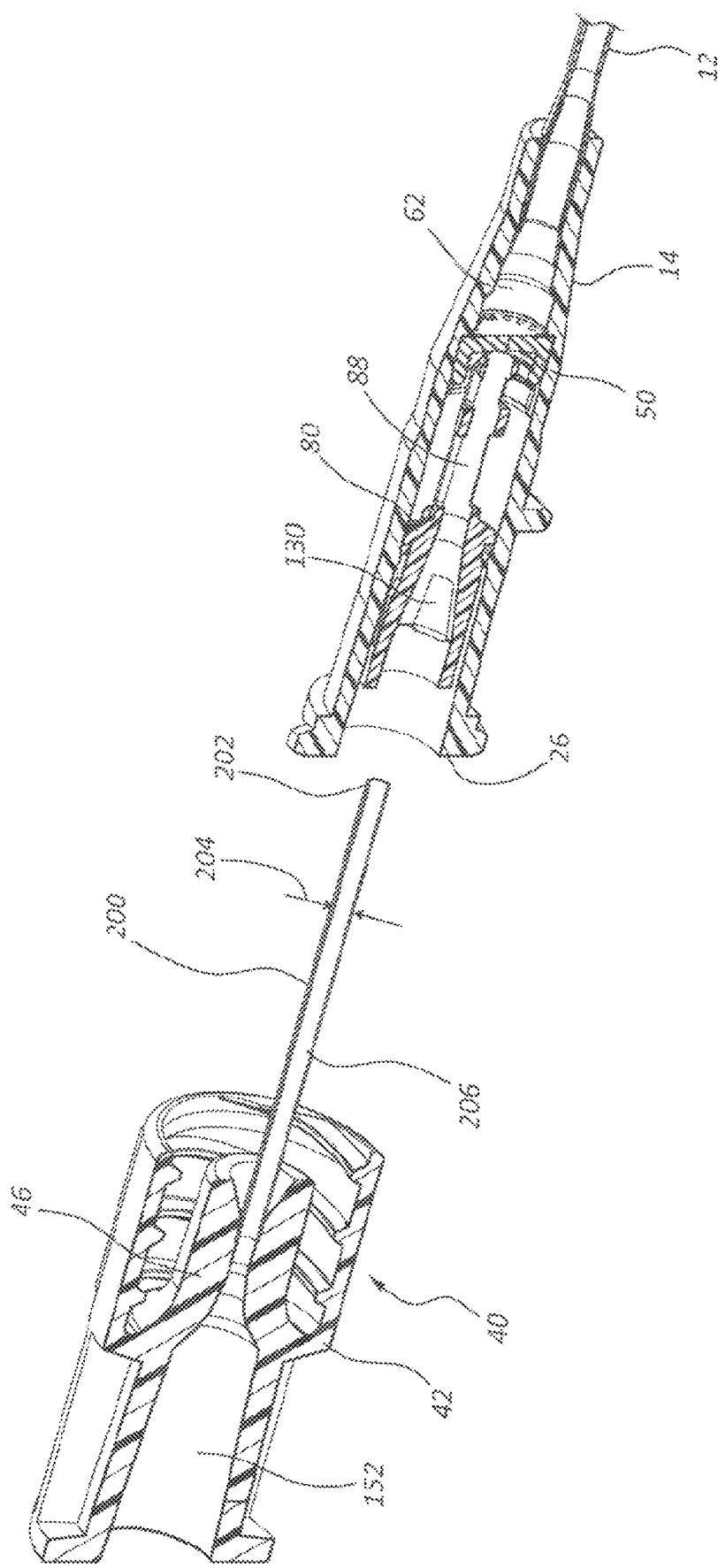
FIG. 9A is a cross-section view of yet another activator attachment prior to its connection to a catheter adapter, according to some embodiments.
Figure 9B:
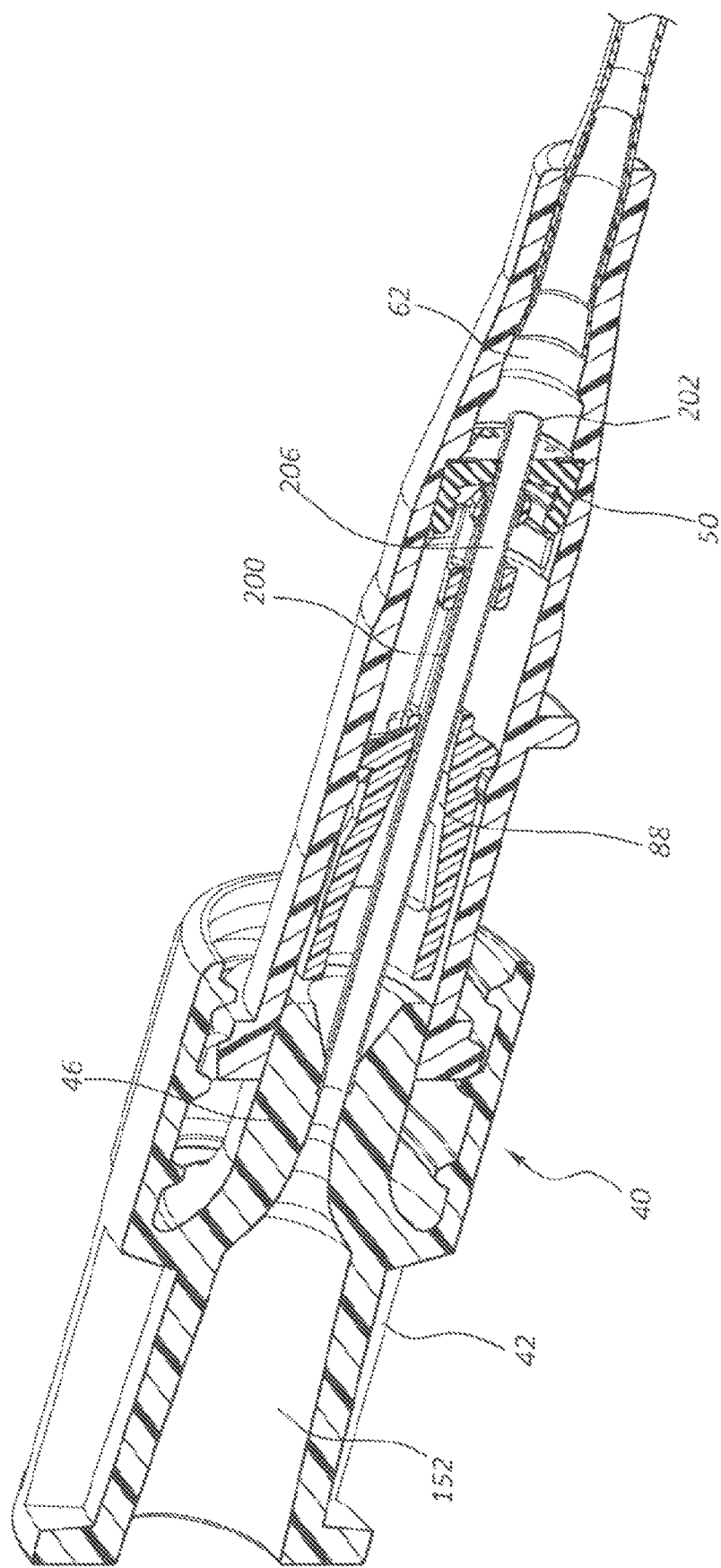
FIG. 9B is a cross-section view of the activator attachment and catheter adapter of FIG. 9A after the activator attachment is fully connected to the catheter adapter, according to some embodiments.

Reference will now be made to FIGS. 9A and 9B, which illustrate another example of an activator attachment 40 in accordance with some embodiments. As shown in FIG. 9A, the activator attachment 40 can include a cannula 200 that is connected to the probe member 46. The activator attachment 40 and cannula 200 can be configured so that when the activator attachment 40 is connected to a catheter adapter 14, the probe member 46 of the activator attachment 40 does not advance the septum activator 80. Additionally, the activator attachment 40 and cannula 200 can be configured so that the cannula 200 can extend through the inner lumen 88 of the septum activator 80 and through the septum 50, opening the septum 50. Thus configured, the activator attachment 40 can bypass the septum activator 80 and open a fluid path between the distal fluid chamber 62 of the catheter adapter 14 and the inner lumen 152 of the activator attachment 40.

Referring to FIG. 9B, in some embodiments, the inner lumen 206 of the cannula 200 can communicate with the inner lumen 152 of the activator attachment body so that fluid can flow through the cannula 200 into the inner lumen 152 of the activator attachment body. The cannula 200 can have a length greater than the combined length of the septum activator 80 and the barrier surface 52 of the septum 50. Thus, the cannula 200 can have a length configured to extend through the septum activator 80 and through the septum 50 when the probe member 46 is inserted into the proximal opening 26 (shown in FIG. 9A) of the catheter adapter 14. Moreover, the cannula 200 can have an outer diameter 204 less than the smallest inner diameter of an inner lumen 88 of the septum activator 80 so that the cannula 200 can be inserted through the inner lumen 88 of the septum activator 80. In some embodiments this outer diameter 204 is constant over the entire length of the cannula 200. In other embodiments, this outer diameter 204 is constant over a portion of the length of the cannula 200. This portion can include the portion of the cannula 200 that extends through the portion of the septum activator 80 that includes the smallest inner diameter or other inner dimensions. Additionally, the cannula 200 can include a blunt distal end 202 so that it does not damage the flexible septum 50.

As further shown in FIG. 9B, the probe member 46 can have a length that is not sufficiently long enough to contact the contact surface 140 of the septum activator 80 when the probe member 46 is inserted into the catheter adapter 14. For example as shown, the connector portion 42 can extend farther than the probe member 46, which is thus a blunt probe member or blunt male luer. As such, the probe member 46 cannot advance the septum activator 80. Rather, the septum activator 80 remains in place, while the cannula 200 extends through the septum activator 80 and the septum 50.

In light of the foregoing, it will be understood that the activator attachment 40 can provide various benefits. For example, the activator attachment 40 can activate the blood control valve by pushing the septum activator 80 through the septum 50 thus creating and open flow path. At this point, blood is allowed to leak through the septum, which can be useful for blood collection and sampling. The activator attachment 40 can also create a direct path for the guide wire to be inserted into the septum 50 into the vein, bypassing the large vents, as it is guided down the center of the entire catheter assembly 10 and can be more easily inserted into the vein, during a MST procedure. Additionally, in some embodiments, the activator attachment 40 can assist to automatically close the blood control valve after the activator attachment is through the use.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly system comprising:
   a catheter adapter having an inner lumen extending between a proximal opening of the catheter adapter and a distal end of the catheter adapter, the proximal opening of the catheter adapter having an inner diameter;
   a septum disposed within and selectively sealing the inner lumen;
   a septum activator disposed within the inner lumen at a location proximal to the septum and having a proximal opening, a distal end, and an inner lumen extending through the proximal opening of the septum activator and the distal end of the septum activator, wherein the proximal opening of the septum activator is formed by a wall, wherein the septum activator further comprises a flow diversion channel extending through the wall between the proximal opening and the distal end of the septum activator, the proximal opening of the septum activator having an inner diameter that is less than the inner diameter of the catheter adapter, the septum activator being configured to advance distally through a slit in the septum; and
   an activator attachment comprising:
      a body configured to attach to a proximal end of the catheter adapter;
      a probe member that extends from a distal end of the body, the probe member having an outer diameter that is less than the inner diameter of the proximal opening of the catheter adapter and greater than the inner diameter of proximal opening of the septum activator, such that the probe member is configured to insert within the proximal opening the catheter adapter; and
      an extension member that extends from a distal end of the probe member, the extension member having an outer diameter that is less than the inner diameter of the proximal opening of the septum activator, such that the extension member is configured to insert within the proximal opening of the septum activator such that a contact surface is formed between the distal end of the probe member and a proximal end of the extension member, the contact surface forming a distal-facing ridge that extends radially outward between the proximal end of the extension member and the distal end of the probe member, the contact surface being configured to contact a proximal end of the septum activator when the activator attachment is connected to the catheter adapter thereby forcing the septum activator distally through the septum, wherein an activator attachment lumen extends from a proximal opening formed at a proximal end of the body to a distal opening positioned at a distal end of the extension member, wherein when the extension member is inserted within the proximal opening of the septum activator such that the contact surface contacts the proximal end of the septum activator, the extension member at least partially covers the flow diversion channel.

2. The catheter assembly system of claim 1, wherein a diameter of the activator attachment lumen increases from the distal opening to the proximal opening of the activator attachment lumen.

3. The catheter assembly system of claim 1, wherein the probe member forms a male luer taper.

4. The catheter assembly system of claim 1, wherein the proximal end of the catheter adapter includes a flange and the body includes a collar that extends around the flange to couple the activator attachment to the catheter adapter.

5. The catheter assembly system of claim 1, wherein the catheter adapter forms a female luer fitting and the activator attachment forms a corresponding male luer fitting.

6. The catheter assembly system of claim 5, wherein the female and male luer fittings are luer lock fittings.

7. The catheter assembly system of claim 5, wherein the female and male luer fittings are luer slip fittings.

8. The catheter assembly system of claim 1, wherein a sidewall of the septum activator includes one or more openings and the extension member is configured to completely cover the one or more openings when the extension member is fit within the proximal end of the septum activator.

9. The catheter assembly system of claim 1, wherein a proximal portion of the activator attachment includes a channel portion.

10. The catheter assembly system of claim 9, wherein the channel portion includes one or more grip portions.

11. The catheter assembly system of claim 1, wherein the catheter adapter further comprises a retention groove, wherein the septum activator further comprises a retention spring and a flow deflector, wherein the retention spring comprises an outwardly biased portion configured to compatibly engage the retention groove, wherein the flow deflector is positioned to protrude into a flow path through the catheter adapter.

12. The catheter assembly system of claim 1, wherein the extension member includes one or more interlocking features disposed on an outer surface of the extension member, the one or more interlocking features being configured to insert within the flow diversion channel of the septum activator when the contact surface contacts the proximal end of the septum activator such that, when the activator attachment is withdrawn from within the catheter adapter, the extension member pulls on the septum activator to withdraw the septum activator from the septum.

* * * * *